United States Patent
Luini et al.

(10) Patent No.: US 11,860,099 B2
(45) Date of Patent: Jan. 2, 2024

(54) REAGENTS FOR OPTICAL MICROSCOPY

(71) Applicant: Alda S.r.l., Naples (IT)

(72) Inventors: Alberto Luini, Fossacesia (IT); Vincenzo Manuel Marzullo, Naples (IT); Giuseppe Palumbo, Naples (IT); Federica Liccardo, Mugnano Di Napoli (IT)

(73) Assignee: Alda S.r.l., Naples (IT)

( * ) Notice: Subject to any disclaimer, the term of this patent is extended or adjusted under 35 U.S.C. 154(b) by 737 days.

(21) Appl. No.: 16/625,683

(22) PCT Filed: Jun. 26, 2018

(86) PCT No.: PCT/IB2018/054712
§ 371 (c)(1),
(2) Date: Dec. 21, 2019

(87) PCT Pub. No.: WO2019/003114
PCT Pub. Date: Jan. 3, 2019

(65) Prior Publication Data
US 2020/0141869 A1 May 7, 2020

(30) Foreign Application Priority Data

Jun. 26, 2017 (IT) .................. 102017000071296

(51) Int. Cl.
*G01N 21/64* (2006.01)
*C07K 16/28* (2006.01)
*C07K 17/14* (2006.01)
*G01N 33/533* (2006.01)
*G01N 33/53* (2006.01)
*C07K 16/18* (2006.01)
*C07K 16/30* (2006.01)

(52) U.S. Cl.
CPC ......... *G01N 21/6458* (2013.01); *C07K 16/18* (2013.01); *C07K 16/28* (2013.01); *C07K 17/14* (2013.01); *G01N 33/533* (2013.01); *G01N 33/5306* (2013.01); *C07K 16/30* (2013.01); *C07K 2317/55* (2013.01); *C07K 2319/60* (2013.01)

(58) Field of Classification Search
None
See application file for complete search history.

(56) References Cited

U.S. PATENT DOCUMENTS

| 2011/0294987 A1 | 12/2011 | Kanazaki et al. |
| 2015/0018540 A1* | 1/2015 | Prakash ............... C12N 15/111 536/24.5 |
| 2015/0368612 A1* | 12/2015 | Palucka ............... A61K 45/06 435/325 |

FOREIGN PATENT DOCUMENTS

| WO | WO 2017/044894 A2 | 3/2017 |
| WO | WO 2017/044894 A3 | 3/2017 |

OTHER PUBLICATIONS

Shapley "peptides and proteins" accessed from butane.chem.uiuc.edu on Jul. 8, 2022 (Year: 2011).*
Ryoji Abe et al "Ultra Q-bodies: quench-based antibody probes that utilize dye-dye interactions with enhanced antigen-dependent fluorescence," Scientific Reports, vol. 4, Apr. 11, 2014, XP055341111, pp. 1-9.
Scheck et al. "Regioselective Labeling of Antibodies through N-Terminal Transamination," ACS Chemical BIO, American Chemical Society, Washington DC US. vol. 2, No. 4, Apr. 1, 2007, pp. 247-251.
Christopher P Toseland "Fluorescent labeling and modification of proteins," Journal of Chemical Biology, Springer Berlin Heidelberg, Berlin/Heidelberg. vol. 6, No. 3, Apr. 13, 2013, pp. 85-95.
Sigma-Aldrich "CF568, Succinimidy Ester," Jan. 1, 2011, pp. 1-3, retrieved from Internet: http:www.sigmaaldrich.com/content/dam/sigma-aldrich/docs/Signma/Bulletin/1/scj4600027bul.pdf.
Su-Yau Mao "Biotinylation of antibodies," "7" In: C. Oliver, M.C. Jamur: "Immunocytochemcial methods and protocols Third Edition," Jan. 2010, Humana Press, Brazil, XP009503656, pp. 49-52.
Schuler B et al. "Specific labeling of polypeptides at amino-terminal cysteine residues using Cy5-benzyl thioester," Bioconjugate Chemistry, vol. 13, No. 5, Jul. 18, 2002, pp. 1039-1043, XP002259205.

* cited by examiner

*Primary Examiner* — Adam Weidner
(74) *Attorney, Agent, or Firm* — ASLAN LAW, P.C.

(57) ABSTRACT

An antibody or Fab fragment, wherein at least one amino group of the N-terminal amino acid of the light chain and/or of the N-terminal amino acid of the heavy chain is bound by an amidic bond to a molecule comprising a fluorophore group A, wherein said bond constitutes at least 70% of the total binding of said molecule to said antibody or Fab.

18 Claims, 13 Drawing Sheets

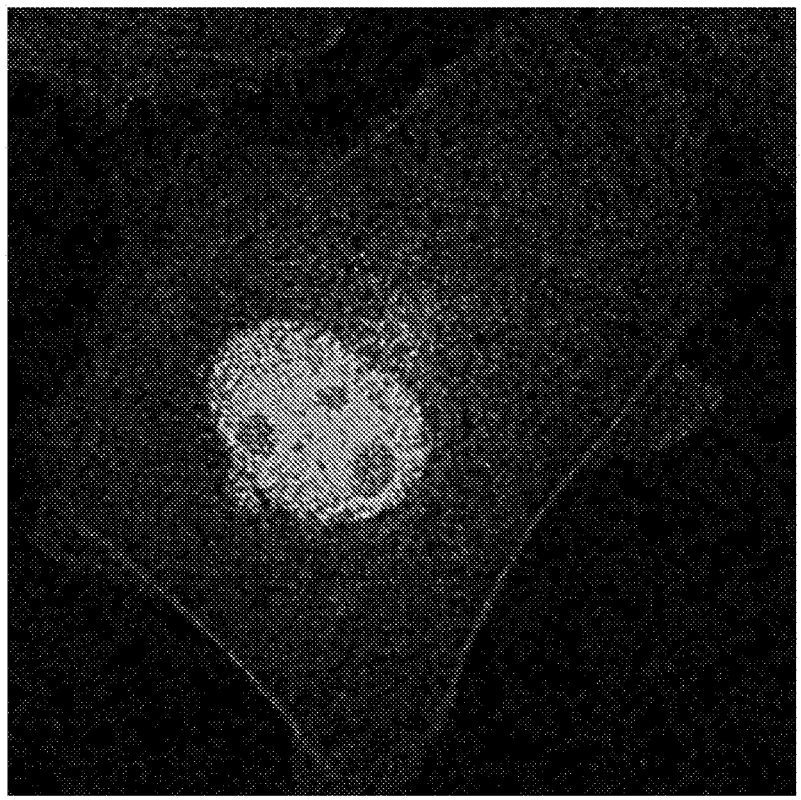
Fig.1A
Fig.1Abis

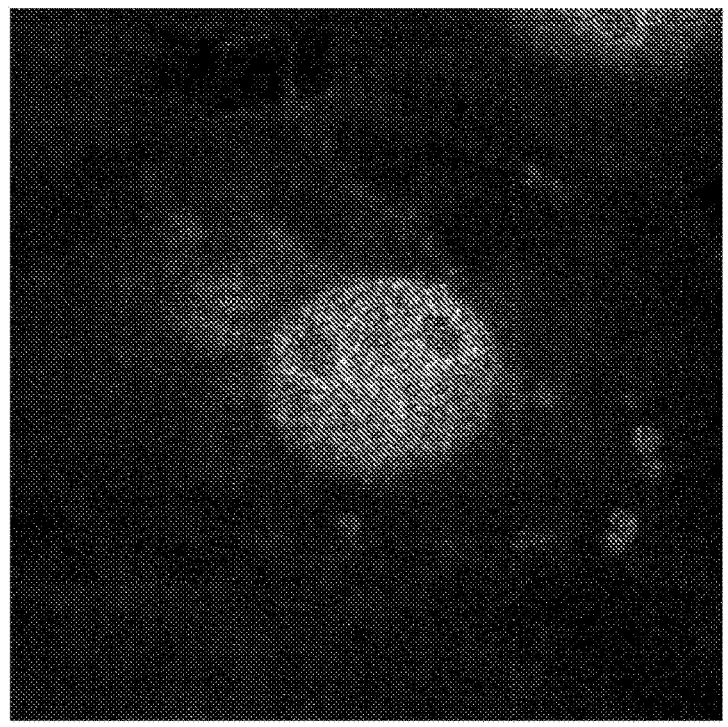
Fig.1B
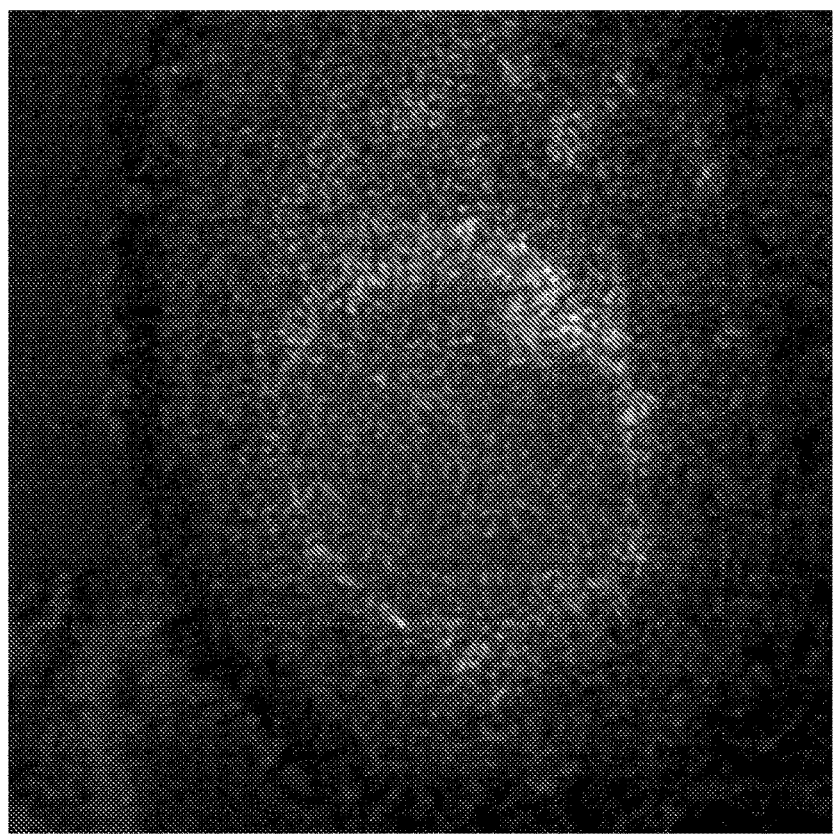
Fig.1Bbis

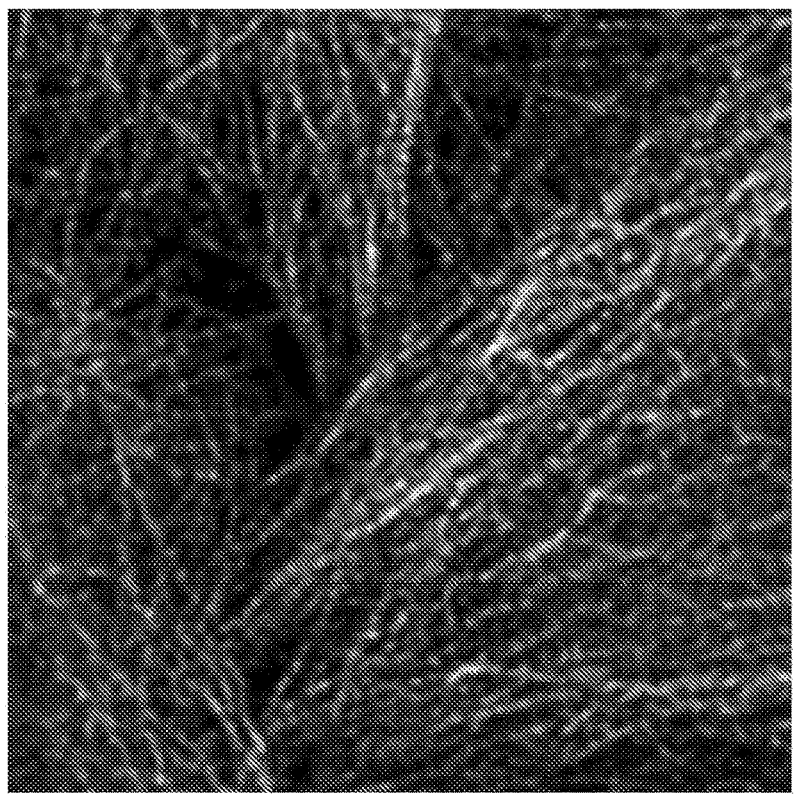
Fig.2A
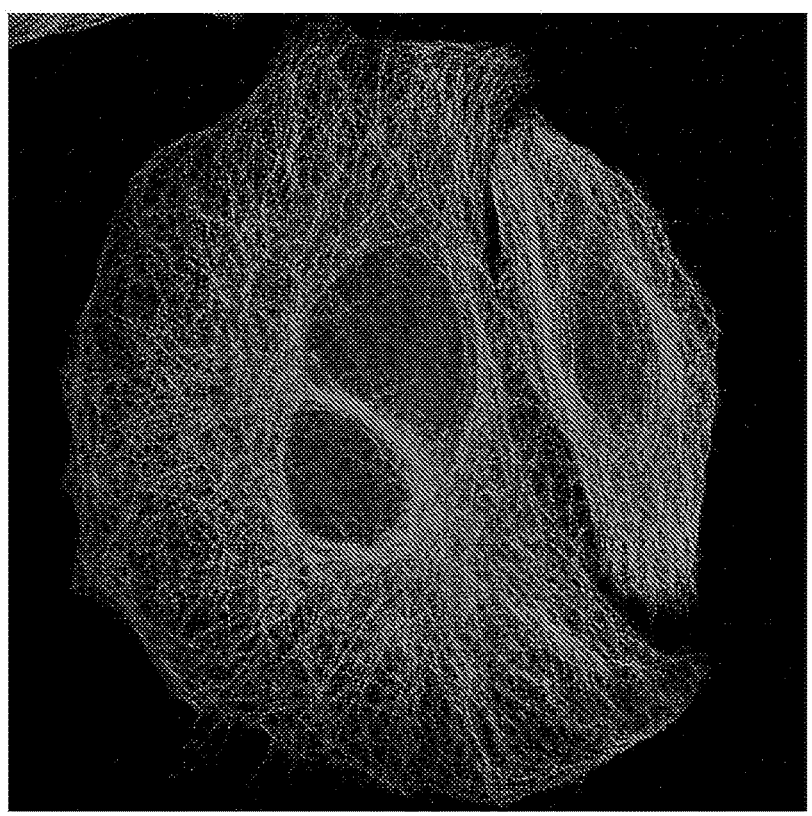
Fig.2Abis

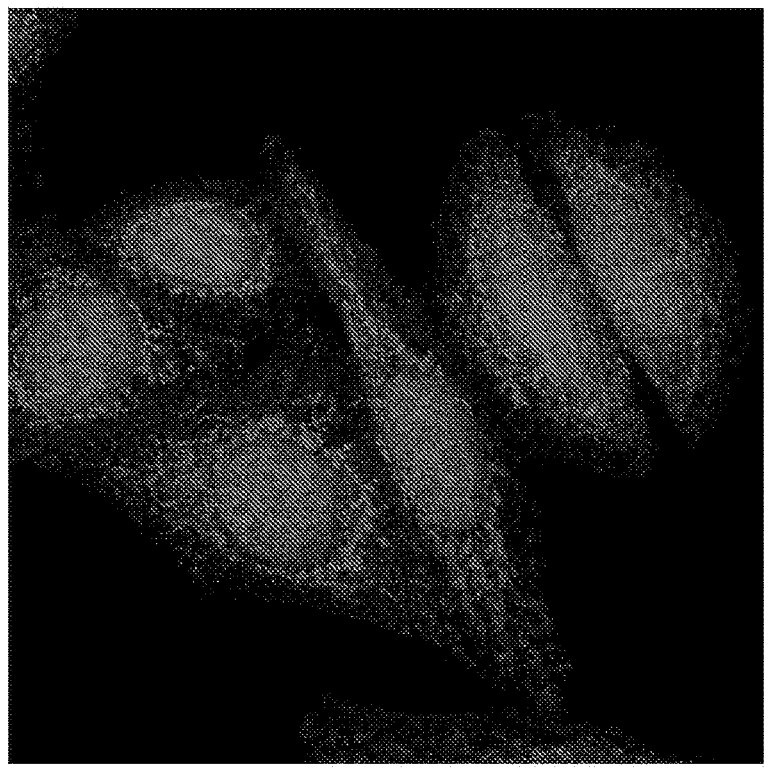
Fig.2B
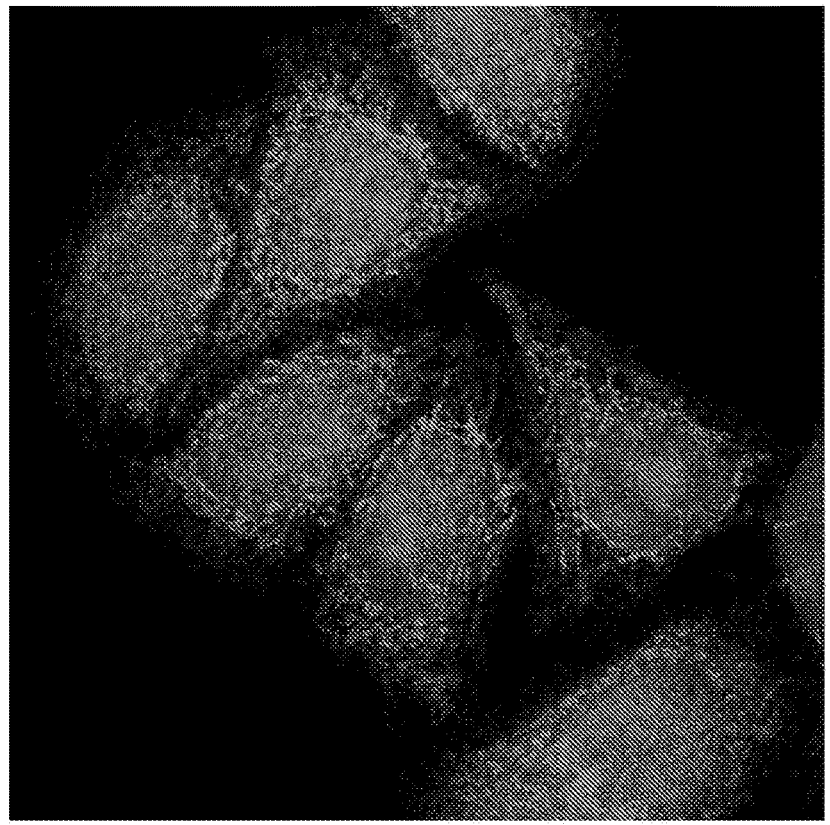
Fig.2Bbis

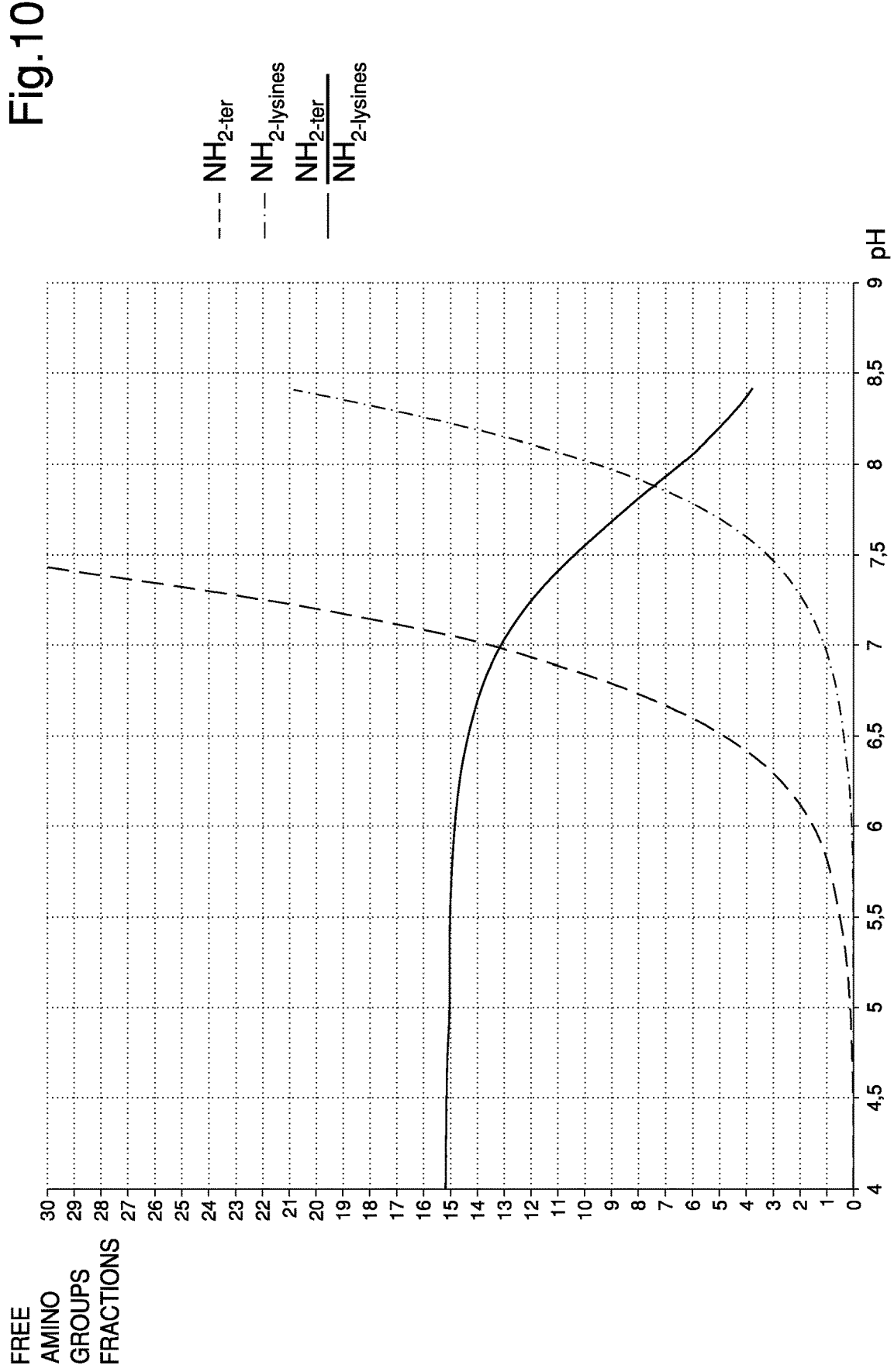

REAGENTS FOR OPTICAL MICROSCOPY

CROSS-REFERENCE TO RELATED APPLICATIONS

This application claims priority to IT Patent Application No. 102017000071296 filed on Jun. 26, 2017, and to PCT Application No. PCT/IB2018/054712 filed on Jun. 26, 2018, the entire contents of which are hereby incorporated by reference.

TECHNICAL FIELD

The present invention relates to the field of immunofluorescence microscopy and, in particular, to new immunofluorescent probes to be used in this technique.

BACKGROUND ART

Immunofluorescence microscopy is a technique which allows displaying specific protein antigens in tissues or cells through the use of antibodies marked with fluorescent molecules, also called immunofluorescent probes, exploiting the ability of antibodies to recognize and bind in a specific way to a protein epitope outside or inside cells. Two main methods can be distinguished for making visible the antigens of interest: direct and indirect immunofluorescence. In direct immunofluorescence, the antibodies directed against an antigen of interest and already conjugated to a fluorophore are made to react with a section of tissue or cells where they specifically bind to the protein of interest. In the case of indirect immunofluorescence, however, the antibody specific to the antigen of interest is made to react with the sample to be analyzed and the binding sites between the antigen and the antibody are highlighted through the use of a second antibody, which binds to the constant portion of the primary antibody and is conjugated to a fluorophore. In both cases, the marked sample is then viewed by fluorescence microscope or confocal microscope. In particular, the sample is illuminated with a beam of light at a specific wavelength which is absorbed by the fluorophore, which re-emits light at a longer wavelength than that of the absorbed light. The exciting light is separated from the emitted light thanks to the use of a filter and the fluorescent signal is therefore displayed at the antigen.

Compared to electronic microscopy, the big advantage of this technique is that it can be used in ex vivo systems.

The primary or secondary antibodies commonly used in immunofluorescence are conjugated to fluorophore via amino or sulphydryl groups of lysine residues or lateral chain cysteine. However, the bonding to lysine residues, which is the most widely used technique, does not permit controlling the exact positioning and number of fluorophore molecules which bind to the antibody, resulting in a heterogeneous mixture of marked antibodies (Wang et al, Protein Sci 2005, 14: 2436). Furthermore, marking lysine residues close to the antigen binding site may lead to a steric encumbrance of the antigen binding site and consequent loss of antibody binding capacity.

Another problem encountered in the marking of antibodies, particularly monoclonal antibodies, is the non-specific binding of fluorophore to hydrophobic portions of the antibody. Therefore, when the marked antibody is used in tissue or cell microscopy analysys techniques, the non-specific binding is hydrolyzed and the fluorophore spreads in the incubation solution, generating a background signal that leads to loss of specificity.

In order to overcome these drawbacks, specific site marking techniques have been developed by introducing into the antibody cysteines with free sulphydryl groups at the terminal C extremity, which are however located at a distance from the antigen binding site.

Among the known marking techniques, the working pH plays a crucial role in the control of selectivity in the conjugation of succinimide esters with terminal amino groups present on the antibody.

In detail, the pH values, at which the amino groups present in a protein are divided into equal quantities in protonated-inert form and in deprotonated-reactive form, correspond numerically to the relative value $pK_n$. At this pH value the two protonated/deprotonated forms exist under conditions of rapid dynamic equilibrium.

In this respect, the methods of acylation of the terminal amino with respect to the amino groups of the lysine residues are currently being studied in order to increase conjugation selectivity.

As previously mentioned, the amino groups present in an antibody can be grouped into two different typologies: the terminal groups (only two) and the numerous $\varepsilon$-amino groups of the lysines. The pK values of the $\varepsilon$-amino terminal groups are generally between 7.5 and 13, while the corresponding terminal groups have an average value of around 7.5.

With higher pH values, the majority of amino groups are indiscriminately deprotonated and consequently reactive.

In this condition, although the reaction yield is extremely high, the selectivity of the coupling with respect to the terminal amino groups is strongly reduced.

In the face of these conditions, the conjugation selectivity with respect to terminal amino groups is severely limited, and on the contrary the possibility of uncontrolled conjugation of lysine residues present on the lateral chain of the antibody is high.

In this regard, the conjugations not required at the level of the $\varepsilon$-amino groups of lysines, certainly present in the protein to be derivatized, are extremely numerous.

It is easy to appreciate how this problem has only been partially solved to date. In fact, there is a particular need to have realistic measurements of the amino groups available for conjugation according to the pH values to which the antibody is subjected during the reaction in order to ensure high conjugation specificity.

Directing the conjugation towards a particular type of amino group, in particular terminal groups, while discriminating against the other type, i.e. the $\varepsilon$-amino groups of lysine, means raising the selectivity of the reaction and this is not an easy problem to solve.

In recent years, optical microscopy has made considerable progress from an instrumental point of view, with a significant increase in performance in terms of lateral resolution. For example, super-resolution microscopes have been developed that have 2 to 10 times the resolution of a normal optical microscope. These instruments allow using optical microscopy to study sub-cellular structures, even very small ones close to each other. For example, STED microscopy can resolve nanoscopic objects of around 30-50 nm, while the various techniques based on stochastic reconstruction achieve a lateral resolution of 10-40 nm. Furthermore, the combination of stochastic and deterministic techniques (MINIFLUX, Hell 2016) currently makes it possible to distinguish 1 nanometer large particles from 3 nanometer ones.

However, technological advances at instrumental level have highlighted the major limitations of fluorescent systems commonly used in immunofluorescence procedures, which have proved inadequate for achieving the full potential of modern microscopes.

In fact, despite currently-used fluorophores being designed to have optimal photo-physical characteristics, the antibodies to which they are linked have dimensions which are of the same magnitude as the sub-micrometric objects under observation. Furthermore, as discussed above, the binding of the fluorophore to the antibody takes place in sites distant from the antigen binding site and therefore prevents the positioning of the fluorescent signal in the proximity of the antibody.

In recent years, attempts have been made to improve the performance of the fluorescent recognition element through the development of alternative systems to antibodies, smaller in size than these, mainly marked nanobodies and aptamers.

However, the use of these fluorescent probes has several limitations, including a lack of commercial availability. Furthermore, although the size of the nanobodies is smaller than that of common immunofluorescence antibodies, it is not possible in this case to obtain the positioning of the fluorophore at a short distance from the epitope. The aptamers, on the other hand, allow marking at a few Ångström from the epitope, but have in turn the limitation of being able to be used only for extra-cellular epitopes, while most of the epitopes of interest have an intracellular localization.

There is therefore a need to develop new immunofluorescent probes to overcome the problems discussed above.

SUMMARY OF THE INVENTION

The present inventors have developed a technique for the regioselective marking of antibodies or Fab fragments at the level of the heavy and/or light chain N-terminal amino group and have found that antibodies selectively marked through an amide bond to molecules comprising fluorophore groups are stable and have homogeneous characteristics in terms of positioning and extent of the bond with the fluorophore.

Furthermore, the present inventors have found that when the fluorophore has certain characteristics of flexibility and lipophilicity, the antibodies or Fab fragments marked according to the invention maintain avidity for the antigen and are suitable for use in microscopy techniques, in which they permit obtaining a surprisingly high level of resolution, thanks to the proximity between the site of bonding with antigen and fluorophore and the selectivity of the fluorophore bond.

Moreover, in the case of Fab fragments, as will be demonstrated in the experimental examples, the inventors found that the small size of the conjugates obtained, about one sixth compared to those of conventional probes, not only generate a high density and specificity of staining, but allow the localization of the probe in cell regions where the conventional marker has no access, for example in cell midbodies.

Therefore, a first object of the present invention is an antibody or a Fab, preferably a Fab, capable of emitting fluorescence following light stimulation, in which the amino group of the N-terminal amino acid of the light chain and/or of the N-terminal amino acid of the heavy chain is bound by an amidic bond to a molecule comprising a fluorophore group A, wherein said bond constitutes at least 70% of the total binding of said molecule to said antibody or Fab.

A second object of the present invention is the use of an antibody or a Fab in accordance with the first object of the invention, as an immunofluorescent probe, preferably by direct immunofluorescence, in fluorescence microscopy techniques, preferably super-resolution confocal fluorescence microscopy.

A third object of the present invention is a method for the preparation of the antibody or Fab in accordance with the first object of the invention comprising the reaction between an antibody or Fab fragment and a molecule comprising a fluorophore group A and a —COOB group, in which the group B is a group having electrophilic characteristics capable of reacting with the nucleophile protein groups, preferably selected from among the following: 1-pyrrolidinyl-2.5-dione and 1-pyrrolidinyl-3-sulfonyl-2.5-dione with the following formula respectively

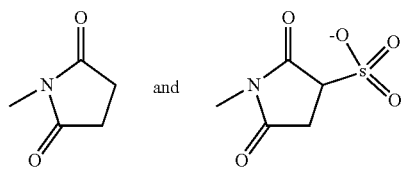

DESCRIPTION OF THE FIGURES

The FIGS. 1A and 1Abis represent images of COS7 cells obtained by confocal microscopy following incubation with Fab from rabbit polyclonal directed against the BARS protein prepared as described in example 1a and marked with CF568 fluorophore as described in example 3a (INV), in which the succinimide ester is 1-pyrrolidinil, 2.5-dione and 1-pyrrolidinil, 3-sulfonyl 2.5-dione, respectively.

The FIGS. 1B and 1Bbis represent images of COS7 cells obtained by confocal microscopy following incubation with Fab from rabbit polyclonal directed against the BARS protein prepared as described in example 1a and marked with fluorophore AF647 as described in example 3b (INV), in which the succinimide ester is 1-pyrrolidinil, 2.5-dione and 1-pyrrolidinil, 3-sulfonyl 2.5-dione, respectively.

The FIGS. 2A and 2Abis represent images of Hela cells obtained by confocal microscopy following incubation with Fab from mouse monoclonal directed against the alpha tubulin protein prepared as described in example 1b and marked with CF568 fluorophore as described in example 3c (INV), in which the succinimide ester is respectively 1-pyrrolidinil, 2.5-dione and 1-pyrrolidinil, 3 sulfonyl 2.5-dione.

The FIGS. 2B and 2Bbis represent images of Hela cells obtained by confocal microscopy following incubation with Fab from rabbit polyclonal directed against the AKAP9 protein prepared as described in example 1c and marked with CF647 fluorophore as described in example 3e (COMPARISON), in which the succinimide ester is 1-pyrrolidinil, 2.5-dione and 1-pyrrolidinil, 3-sulfonyl 2.5-dione, respectively.

Figure 3A:
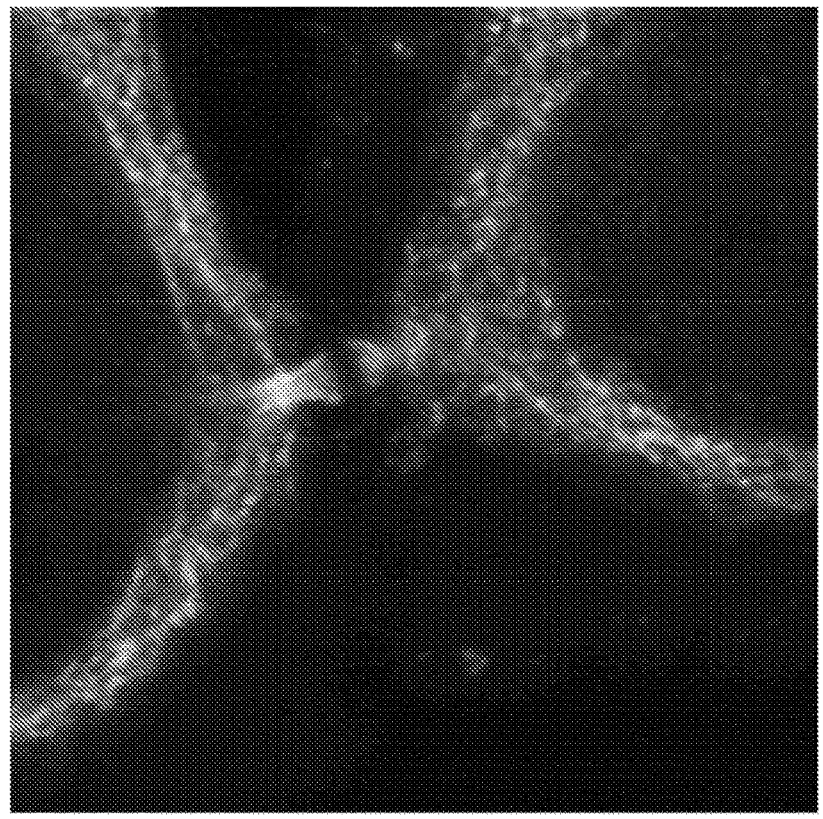
Figure 3B:
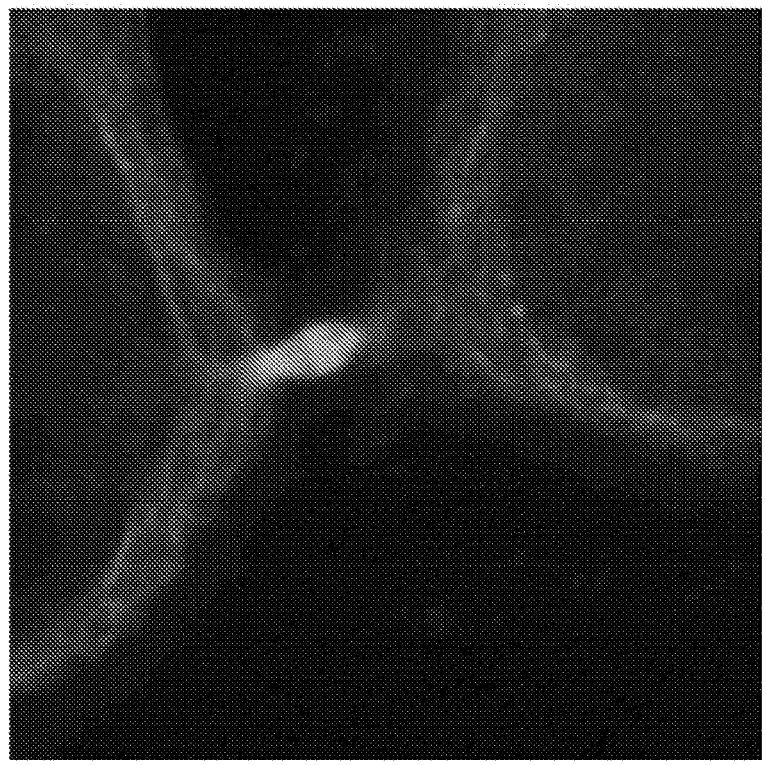

The FIGS. 3A and 3B represent images of Hela cells obtained by confocal microscopy following incubation with Fab from mouse monoclonal directed against the alpha tubulin protein marked with both CF568 fluorophore and AlexaFluor488 (AF488) control fluorophore. The image in FIG. 3A was captured at a wavelength in the range of 490 to 450 nm at which the fluorescent emission comes from the control fluorophore AF488 only. The image in FIG. 3B was captured at a wavelength in the range of 575 to 620 nm at which the fluorescent emission comes from CF568 fluorophore only.

Figure 4A:
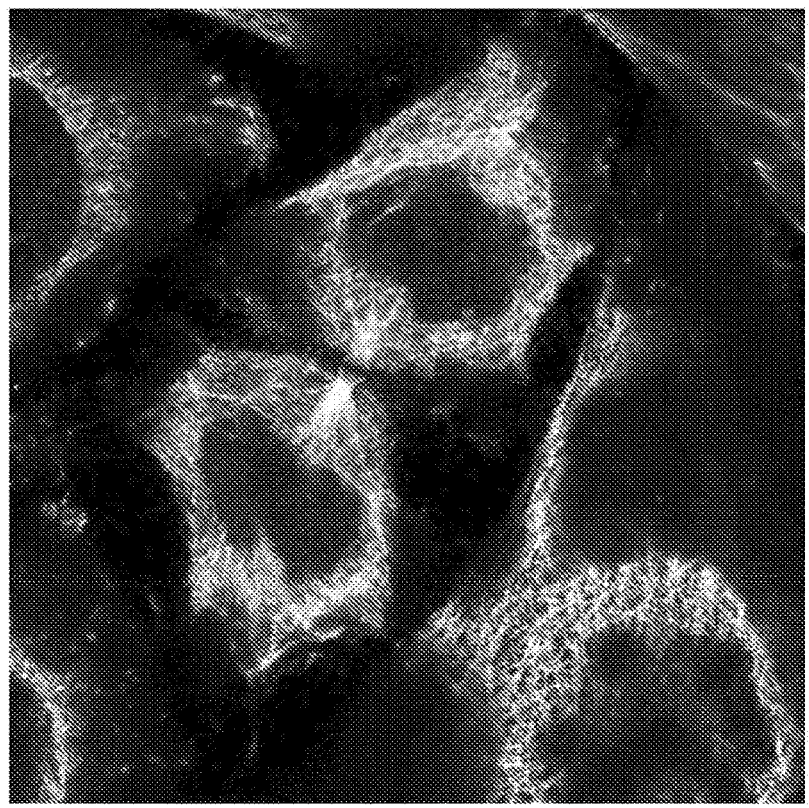
Figure 4B:
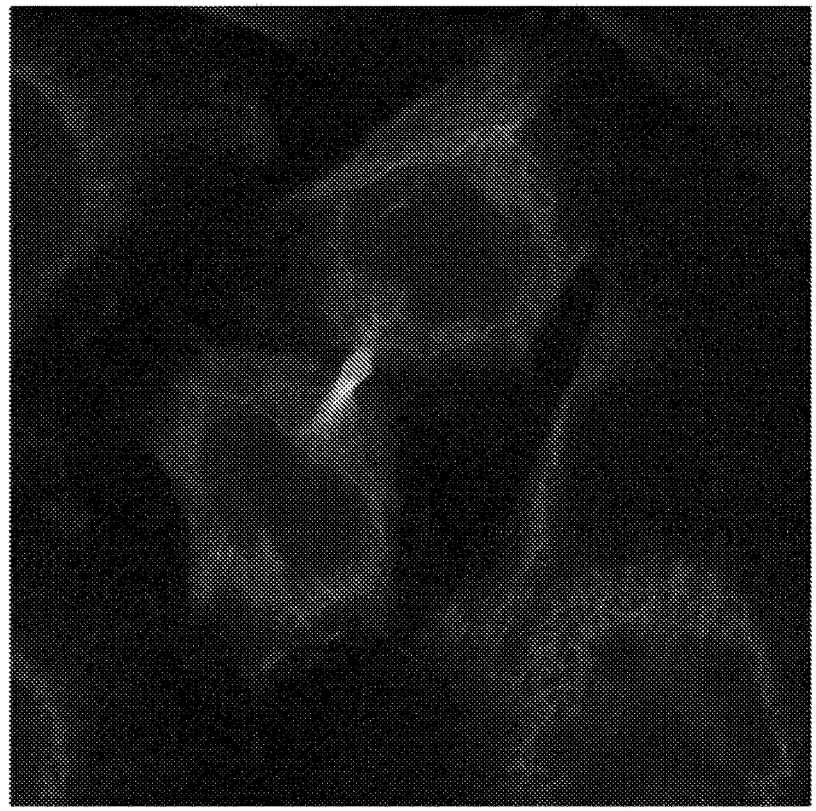

FIGS. 4A and 4B represent images obtained by confocal microscopy of Hela cells following incubation with Fab from mouse monoclonal directed against the alpha tubulin protein marked with both CF568 fluorophore and AlexaFluor488 (AF488) control fluorophore. The image in FIG. 4A was captured at a wavelength in the range of 490 to 450 nm at which the fluorescent emission comes from the control fluorophore AF488 only. The image in FIG. 4B was captured at a wavelength in the range of 575 to 620 nm in which the fluorescent emission comes from CF568 fluorophore only.

Figure 5A:
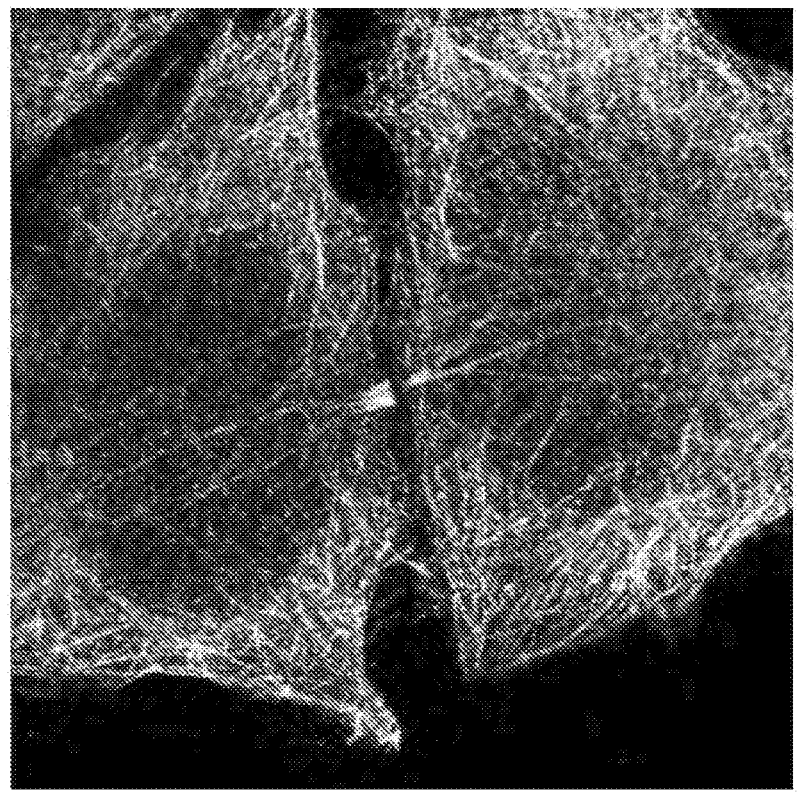
Figure 5B:
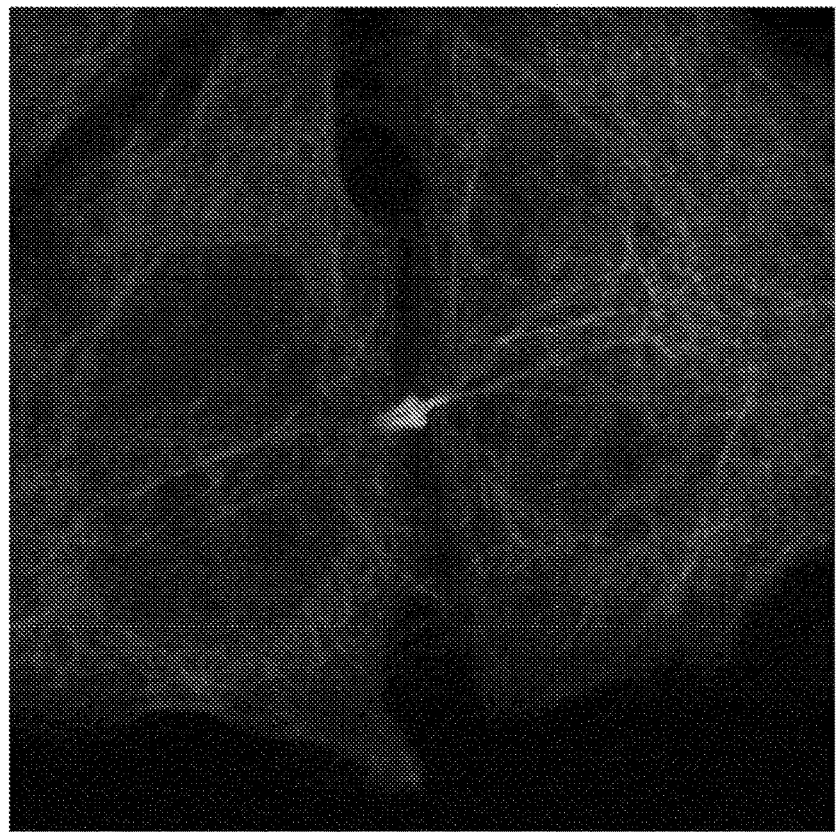

FIGS. 5A and 5B represent images obtained by confocal microscopy of Hela cells following incubation with Fab from mouse monoclonal directed against the alpha tubulin protein marked with both CF568 fluorophore and AlexaFluor488 (AF488) control fluorophore. The image in FIG. 5A was captured at a wavelength in the range of 490 to 450 nm at which the fluorescent emission comes from the AF488 control fluorophore only. The image in FIG. 5B was captured at a wavelength in the range of 575 to 620 nm in which the fluorescent emission comes from the CF568 fluorophore only.

Figure 6A:
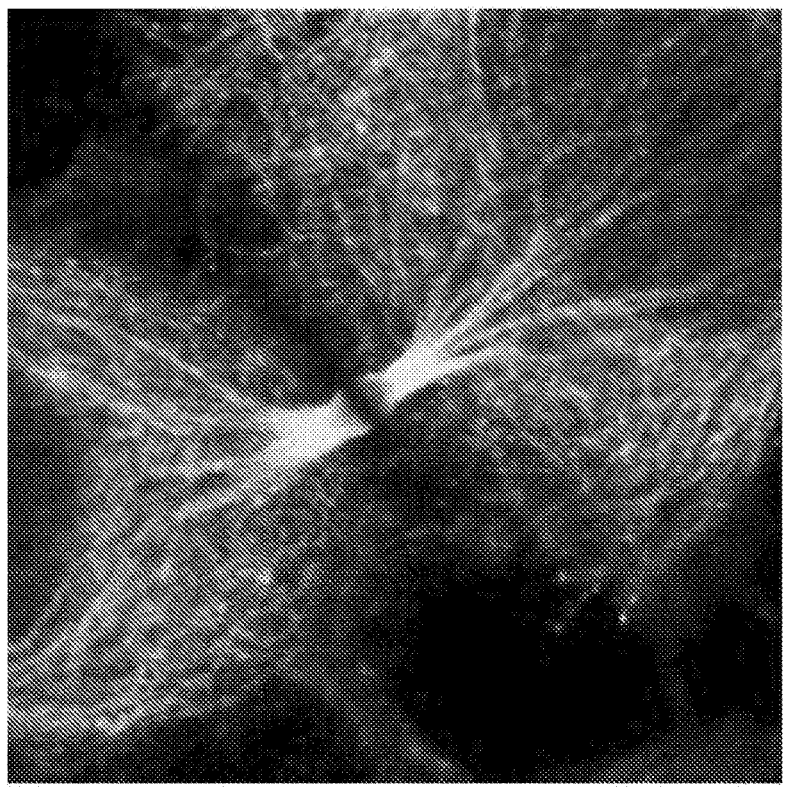
Figure 6B:
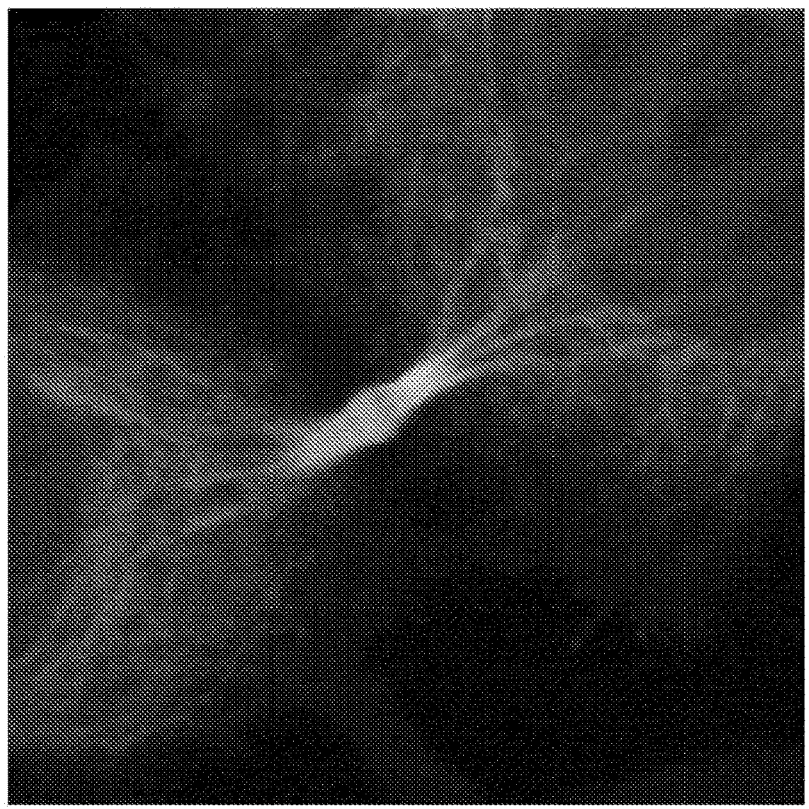

FIGS. 6A and 6B represent images obtained by confocal microscopy of Hela cells following incubation with Fab from mouse monoclonal directed against the alpha tubulin protein marked with both AF647 fluorophore and AlexaFluor488 (AF488) control fluorophore.

The image in FIG. 6A was captured at a wavelength in the range of 490 to 450 nm in which the fluorescent emission comes from the AF488 control fluorophore only. The image in FIG. 6B was captured at a wavelength in the range of 660 to 700 nm in which the fluorescent emission comes from the AF647 fluorophore only.

Figure 7A:
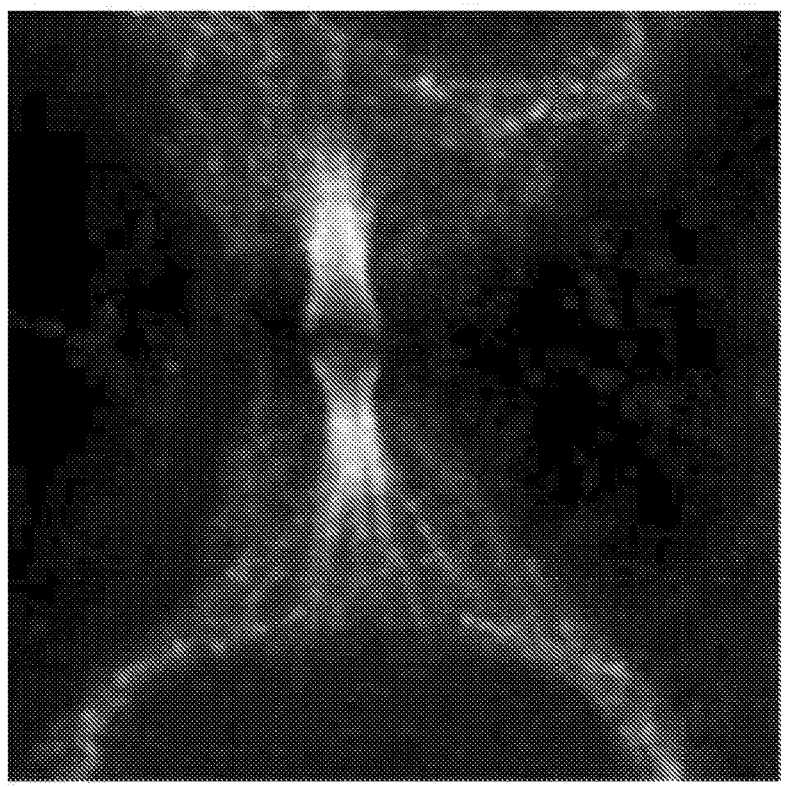
Figure 7B:
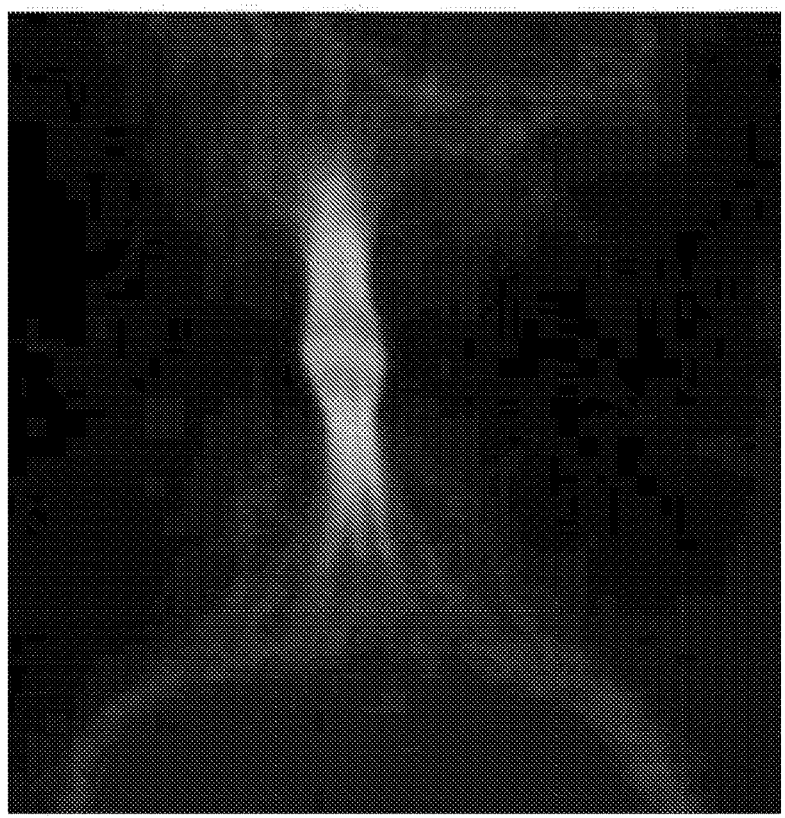

FIGS. 7A and 7B represent images obtained by confocal microscopy of Hela cells following incubation with Fab from mouse monoclonal directed against the alpha tubulin protein marked with both AF647 fluorophore and AlexaFluor488 (AF488) control fluorophore. The image in FIG. 7A was captured at a wavelength in the range of 490 to 450 nm in which the fluorescent emission comes from the AF488 control fluorophore only. The image in FIG. 7B was captured at a wavelength in the range of 660 to 700 nm in which the fluorescent emission comes from the AF647 fluorophore only.

FIGS. 8A, 8B, 8C, 8D represent a comparison of images acquired by STORM technique on an advanced optical platform under SMLM (Single Molecule Localization Microscopy) of a microtubule marked with fluorescent probes in accordance with the present invention.

Figure 9:
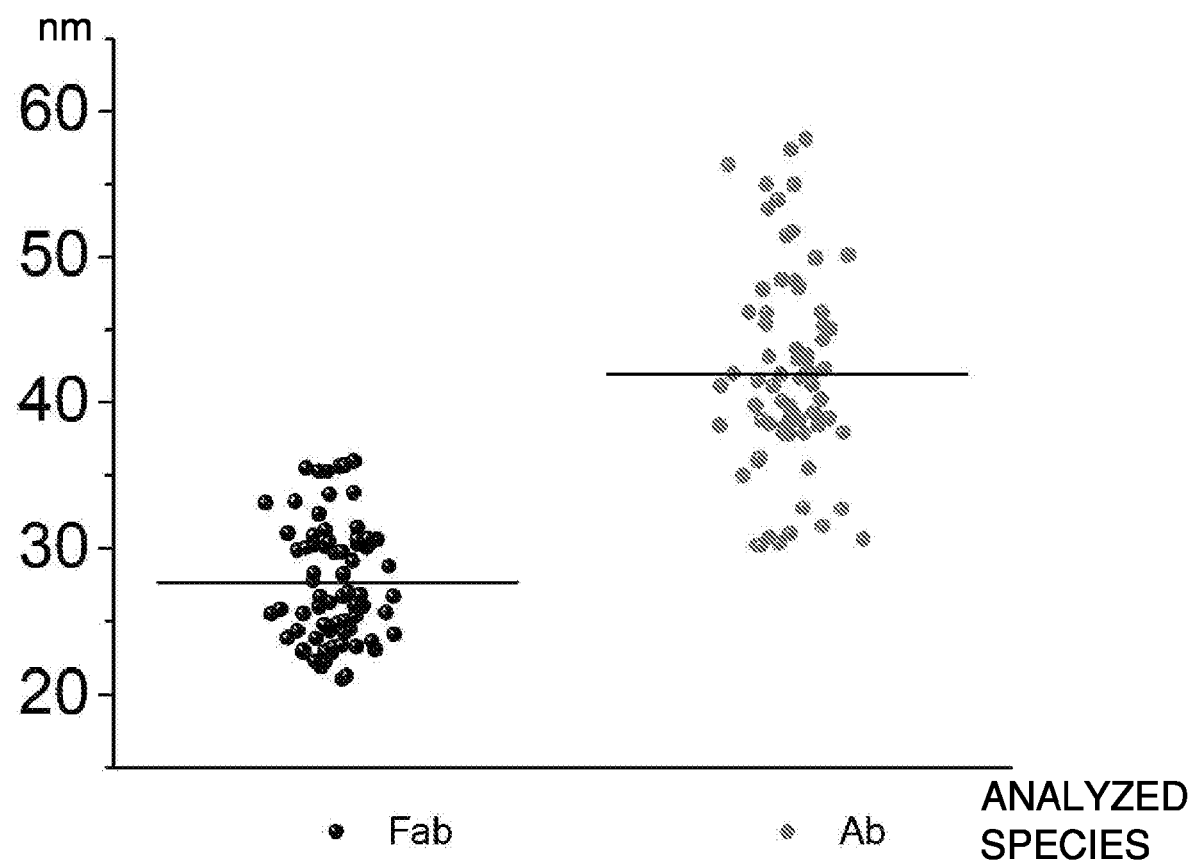

FIG. 9 represents a comparison of the resolution limit obtained through the use of probes in accordance with the present invention and conventional probes. In detail, the average diameter of a microtubule was measured.

The section of the microtubule was quantified by measuring the intensity profile (i.e. number of localizations) along a segment placed perpendicular to the microtubule.

The amplitude value at half the height of this profile was compared and both marking methods were compared.

FIG. 10 represents a graph based on an analysis carried out on a Fab characterized by a terminal amino group with pKa=7.8 and a ε-amino group with pKa=8.89, potentially in competition with each other.

The above figure shows the respective titration curves from which it is possible to evaluate the fractions of the free amino groups, both terminal and ε-amino, at each pH value. Shown at the same time is a further curve representing the variations in the $NH_{2\text{-}ter}/NH_{2\text{-}lysine}$ ratio and by means of which an optimum pH can be selected for its maximization.

It appears evident how the relation between reactive terminal groups and amino groups of lysines tends to increase as the pH values decrease.

Definitions

The Kier flexibility index ($\Phi$), Kier molecular flexibility index, KierFlex,) is a molecular flexibility index, numerically defined by the parameters A, $^1k_{alfa}$ and $^2k_{alfa}$ according to the following relation:

$$\Phi = \frac{^1k_\alpha \cdot {}^2k_\alpha}{A}$$

in which $^1k_{alfa}$ and $^2k_{alfa}$ are parameters which include the contribution of rigid connections, i.e. cycles, unsaturated or hetero-atomic, which do not allow free rotation of the molecular planes along the interatomic axis of the elements of the molecule; and A represents the number of "angles" i.e. atoms of the molecule.

The value of each of the above descriptors is calculated starting with simplified molecular structures, i.e. represented only by the carbon-carbon or carbon-heteroatom connections, thus excluding all carbon-hydrogen connections. Such structures, often referred to in literature as "H-depleted molecular graph" (Kier, (1989), Quant. Struct.—Act. Relat. 8, 221-224), consist of number A "angles" (in vertex literature) and P "edges" (in paths literature).

A is determined by counting the angles of a molecular structure, as shown below:

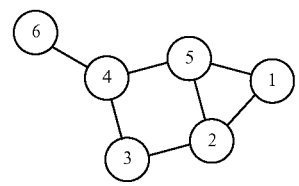

The purpose of the P value is to calculate the indices $^1k_{alfa}$ and $^2k_{alfa}$.

The number of consecutive connections considered as "edges" is defined as "degree" (in literature m). The k index is grade 1 (m=1) if it is between only two vertices, grade 2 if it is between three vertices, and so on. The degree (m) of an index (k) is then referred to the maximum "path" of the P edge, and is expressed as the apex to the left.

As an example, the calculation of $^mP$ referring to the structures of 2,methyl-pentane and linear pentane is shown below:

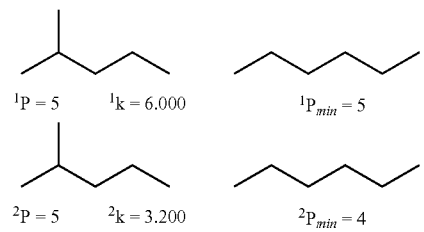

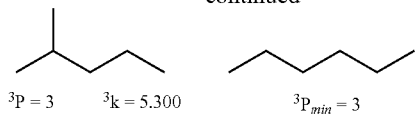

$^3P = 3$    $^3k = 5.300$    $^3P_{min} = 3$

The $^1k_{alfa}$ and $^2k_{alfa}$ indices, of first and second order respectively, are normalized on the alpha factor, which permits including the contribution of possible steric restrictions, different hybridizations (and thus molecular rigidity) and stereo-electronic effects. The alpha values are shown in the table for each carbon hybridization, and for the common heteroatoms included in the organic molecules, as shown below:

| Atom/hybrid | R (Å) | α |
|---|---|---|
| $C_{sp}1$ | 0.77 | 0 |
| $C_{sp}2$ | 0.67 | −0.13 |
| $C_{sp}$ | 0.60 | −0.22 |
| $N_{sp}1$ | 0.74 | −0.04 |
| $N_{sp}2$ | 0.62 | −0.20 |
| $N_{sp}$ | 0.55 | −0.29 |
| $O_{sp}1$ | 0.74 | −0.04 |
| $O_{sp}2$ | 0.62 | −0.20 |
| $P_{sp}1$ | 1.10 | 0.43 |
| $P_{sp}2$ | 1.00 | 0.30 |
| $S_{sp}1$ | 1.04 | 0.35 |
| $S_{sp}2$ | 0.94 | 0.22 |
| F | 0.72 | −0.07 |
| Cl | 0.99 | 0.29 |
| Br | 1.14 | 0.48 |
| I | 1.33 | 0.73 |

The $^1k_{alfa}$ $^2k_{alfa}$ values are calculated as follows:

$$^1K_\alpha = \frac{(A+\alpha)\cdot(A+\alpha-1)^2}{(P^1+\alpha)^2}$$

$$^2K_\alpha = \frac{(A+\alpha-1)\cdot(A+\alpha-2)^2}{(P^2+\alpha)^2}$$

In the formula chosen for the definition of fluorophore flexibility, the k indices considered are only first and second grade.

The logarithm of the water/octanol partition coefficient (A log P) is an approach for the predictive calculation of the water/octanol partition coefficient of small organic molecules.

The method allows obtaining the hydrophilicity value (A log P below zero) and hydrophobia value (or lipophilicity, ALogP above zero) of a chemical structure, and uses the atomic contributions through a parametric model.

The log P value of each molecule is calculated according to the following formula:

$$\log P = \sum_i n_i a_i$$

and is called A log P from the author's name Arup K. Ghose, if calculated using the parameters shown on table 1 published in Ghose, A. K.; Crippen, G. M. J. Comput. Chem. 1986, 7, 565-577.

The partition coefficient of the molecule is considered as the sum of the contribution given by each atom of the structure, calculated according to specific parameters. Such parameters are listed on the above table Ghose, A. K. et al. and are determined on the basis of all possible combinations of chemical surroundings of each atom. Therefore, the polarity of any one atom is variable depending on the atoms to which it is linked, so every possible combination of connections between atoms determines the numerical value of the parameter relating to each atom component of the molecule. The parameterized atoms are: H, C, O, S, N, Si, B, P, Se, F, I, Br, Cl. Such parameters, relating to the A log P calculation method, are extrapolated from the correlation of different coefficients of partition measured experimentally on various model molecules. According to this method, the simulated value of log P, i.e. A log P, can be determined unambiguously for each molecule of interest, regardless of whether the calculated value more or less coincides with the actual coefficient.

TPSA (Topological Polar Surface Area) defines the polar surface area of a molecule using a computational calculation method.

TPSA is based on a cumulative calculation of all topological contributions of each molecular fragment; these contributions have been described in I. Moriguchi, S. Hirono, Q. Liu, I. Nakagome, and Y. Matsushita, Chem. Pharm. Bull. 1992, 40, 127-130 and I. Moriguchi, S. Hirono, I. Nakagome, H. Hiran, Chem. Pharm. Bull. 1994, 42, 976-978, and are summarized on the following table in which the PSA contrib indicates the topological contribution values of the indicated molecular fragments.

| POLAR ATOM SURFACE CONTRIBUTIONS | | |
|---|---|---|
| No. | Atom type | PSA contrib. |
| 1 | [N](−*)(−*)−* | 3.24 |
| 2 | [N](−*) = * | 12.36 |
| 3 | [N]#* | 23.79 |
| 4 | [N](−*)(=*) = * (b) | 11.68 |
| 5 | [N](=*)#* (c) | 13.60 |
| 6 | [N]1(−*)−*−*−1 (d) | 3.01 |
| 7 | [NH](−*)−* | 12.03 |
| 8 | [NH]1−*−*−1 (d) | 21.94 |
| 9 | [NH]=* | 23.85 |
| 10 | [NH2]−* | 26.02 |
| 11 | [N+](−*)(−*)(−*)−* | 0.00 |
| 12 | [N+](−*)(−*)=* | 3.01 |
| 13 | [N+](−*)#* (e) | 4.36 |
| 14 | [NH+](−*)(−*)−* | 4.44 |
| 15 | [NH+](−*) = * | 13.97 |
| 16 | [NH2+](−*)−* | 16.61 |
| 17 | [NH2+]=* | 25.59 |
| 18 | [NH3+]−* | 27.64 |
| 19 | [n](:*):* | 12.89 |
| 20 | [n](:*)(:*):* | 4.41 |
| 21 | [n](−*)(:*):* | 4.93 |
| 22 | [n](=*)(:*):* (f) | 8.39 |
| 23 | [nH](:*):* | 15.79 |
| 24 | [n+](:*)(:*):* | 4.10 |
| 25 | [n+](−*)(:*):* | 3.88 |
| 26 | [nH+](:*):* | 14.14 |
| 27 | [O](−*)−* | 9.23 |
| 28 | [O]1−*−*−1 (d) | 12.53 |
| 29 | [O]=* | 17.07 |
| 30 | [OH]−* | 20.23 |
| 31 | [O−]−* | 23.06 |
| 32 | [o](:*):* | 13.14 |
| 33 | [S](−*)−* | 25.30 |
| 34 | [S] = * | 32.09 |
| 35 | [S](−*)(−*) = * | 19.21 |
| 36 | [S](−*)(− *)(=*)=* | 8.38 |
| 37 | [SH]−* | 38.80 |
| 38 | [s](:*):* | 28.24 |

-continued

POLAR ATOM SURFACE CONTRIBUTIONS

| No. | Atom type | PSA contrib. |
|---|---|---|
| 39 | [s](=*)(:*):* | 21.70 |
| 40 | [P](-*)(-*)-* | 13.59 |
| 41 | [P](-*)=* | 34.14 |
| 42 | [P](-*)(-*)(-*)=* | 9.81 |
| 43 | [PH](-*)(-*) = * | 23.47 | to define TPSA simply calculate the sum of each contribution, according to the following formula:

$$TPSA = \Sigma_{alfa} SA \forall |q_{alfa}| \geq 0.2$$

TPSA therefore represents the sum of the surface area of the atoms of a molecule with an absolute value of partial charges greater than or the same as 0.2 (presumably oxygen and nitrogen with any hydrogen annexed to these) exposed to a solvent and is expressed in $Å^2$ (Ångstrom²).

3D POLAR SASA defines the surface area of the molecule which is accessible to the solvent.

This parameter provides the degree of hydration of the molecule which results in greater stabilization of the conjugate, less tendency to aggregate because it is hydrated and better emission behavior due to increased solvation. Furthermore, the lesser tendency to interact with parts of the fragment also results in a significant increase in avidity because the fluorophores do not collapse on the FAB recognition regions.

The algorithm for the calculation of the 3D polar SASA value allows obtaining the surface fraction of the molecule which cannot be included, due to steric issues, in the hydration sphere of the solvent. The calculation is made on the basis of the Wan der Wals surfaces of both the solvent and the solute. The contribution of atomic fragments is tabulated in Ferrara P. et al., (2002), PROTEINS: Structure, Function, and Genetics, 46, 24-33.

For the calculation of the 3D polar SASA value, the sum of the atomic contributions to the solvation of the molecule is considered. For the calculation of the numerical value, the solvation area is made to coincide with the actual energy value for this solvation, having made the initial assumption that these values are linearly dependent. The value can be calculated using the following algebraic expression:

$$3D \ polarSASA \sum_{i=1}^{M} \sigma_i A_i(r)$$

where $\sigma_i$ is the coefficient of the "weighted" contribution of the atom i (see table below) and $A_i(r)$ is the area fragment with which such atom contributes.

$A_i(r)$ is calculated with the following expression:

$$A_i(r) = S_i \prod_{j \neq i}^{M} [1 - p_i p_{ij} b_{ij}(r_{ij})/S_i]$$

$S_i$ is calculated according to the following expression $$S_i = 4\pi(R_i + R_{probe})^2$$

$b_{ij}(r_{ij})$ is:
0 if $r_{ij} > R_i + R_j + 2R_{probe}$
or $\pi(R_i + R_{probe})(R_i + R_j + 2R_{probe} - r_{ij})[1 + (R_j - R_i)r_{ij}^{-1}]$
in all the other cases.

Rprobe=1.4 Å
$p_{ij}$=0.8875 if the atoms being considered are bonded covalently or
$p_{ij}$=0.3516 in all the other cases.
$R_{min}$, $R_i$, $p_i$ and $\sigma_i$ are tabulated in Ferrara P. et al., mentioned above.

Calculating the formulas indicated above, the 3D polar SASA parameter can be univocally defined.

For the purposes of the present invention, the Kier flexibility index ($\Phi$) and the polar surface area (TPSA) have been calculated using Spartan '15 software (Wavefunction Inc., Pipeline Pilot 2016 Biovia, MOE, CCG).

To calculate the total number of hydrogen bond acceptor atoms (Num_H_Acceptors) Pipeline Pilot software was used (Dassault Systèmes BIOVIA, Pipeline Pilot, R2 version, San Diego: Dassault Systèmes, 2018-Warr W. A. (2012) Scientific workflow systems: pipeline Pilot and KNIME. J. Comput. Aided Mol. Des., 26, 801-804).

With such parameter is associated the polarity of the molecule, and therefore its solubility in water medium, an important aspect considering the reaction conditions described below.

The term "fluorophore group" according to the present invention indicates an atom or a functional group capable of absorbing energy at a specific wavelength and re-emitting fluorescence. The different types of fluorophores are characterized by different absorption and emission spectra.

The term "Fab" or "Fab antibody fragment" according to this invention means a proteolytic fragment of an antibody molecule comprising an entire light chain coupled to a heavy chain fragment containing the variable domain binding the antigen and a portion of the constant domain. Preferably, the Fab fragment according to the invention is monovalent, so it is a fragment that does not comprise the hinge region or may result from the breaking of the sulfide bonds in a fragment comprising the hinge region and have a free sulfide group and a single antigen binding site.

Several Fab fragments can be obtained depending on the proteolytic enzyme used for the digestion of the antibodies from which they derive.

For example, the digestion of an antibody with papain generates monovalent fragments, the digestion of same with pepsin generates bivalent fragments and that with ficin generates bivalent or monovalent fragments depending on the reaction conditions. For the purpose of this invention, disulphide bonds of bivalent fragments are preferably reduced in order to obtain a monovalent Fab.

DESCRIPTION OF THE INVENTION

As described above, the present inventors have developed a method for the regioselective marking of the N-terminal amino group of antibodies or Fab antibody fragments with a molecule comprising a fluorophore group. This method makes it possible to obtain an immunofluorescence probe which is stable over time and has homogeneous characteristics in terms of positioning and intensity of the fluorophore signal. The binding of the fluorophore at the level of the N-terminal amino groups allows its positioning at a very close distance, around 1-2 nm, from the antigen of interest. Despite this proximity, inventors have found that the selection of fluorophore and linkers with specific characteristics prevents fluorophore from interfering with the binding of the antibody or Fab with the antigen and keeps the avidity of epitope binding intact. The marked antibodies and Fabs obtained by the method developed by the inventors can be used as direct fluorescent probes under optical microscopy, allowing a higher resolution to be obtained compared to probes used in direct or indirect conventional fluorescence techniques. In particular, this property is particularly advantageous in the case of super resolution optical microscopy where the fluorescent probes available to date have numerous functional limitations and remain inadequate for achieving the full resolution potential of the microscope. Furthermore, in the case of marked Fabs, the small size of the probe to which the invention refers enables it to be located in cellular regions where the conventional marker does not have access, for example in cellular midbodies.

Therefore, a first object of the present invention is a antibody or Fab antibody fragment, preferably a Fab antibody fragment in which at least one amino group of the N-terminal amino acid of the light chain and/or of the N-terminal amino acid of the heavy chain is bound by an amidic bond to a molecule comprising a fluorophore group A, wherein said bond constitutes at least 70% of the total binding of said molecule to said antibody or Fab.

Preferably, said fluorophore group A is the only fluorophore group bound to said antibody or Fab.

Preferably, the aforementioned binding is selective at N-terminal amino groups level, in particular it constitutes at least 80%, 85%, 90%, 95% or 98% of the total binding of said molecule to said antibody or Fab. The lack of non-specific binding sites or easily hydrolyzable bonds prevents the formation of non-specific fluorescence when the marked antibody or Fab comes into contact with the sample to be analyzed and increases the sensitivity and intensity of the fluorescent signal which is concentrated in the proximity of the antigen.

The above Fab fragment derives preferably from the digestion of an antibody with papain, pepsin or ficin, more preferably papain or ficin. The Fab fragment is preferably monovalent, i.e. it has only one antigen binding site.

The antibody or the Fab according to the invention can be/derive from a monoclonal or polyclonal antibody, between which the preferred is a monoclonal antibody.

According to a preferred embodiment, the aforementioned polyclonal antibody is a rabbit polyclonal antibody, preferably of the IgG2b type, and the aforementioned monoclonal antibody is a mouse antibody, preferably of the IgG1 type.

The present inventors have found that the presence of a linker between the antibody/Fab and the fluorophore and/or the selection of fluorophore with specific characteristics permits keeping intact the avidity of the antibody with the antigen and therefore obtaining fluorescent probes with high signal efficiency.

Preferably, in the antibody or Fab fragment according to the invention, said amino group of the N-terminal amino acid of the light chain and/or of the N-terminal amino acid of the heavy chain is bound by an amidic bond to a Z group with formula:

—CO—(W)$_n$-A wherein:
n is 0 or 1,
A is a fluorophore group,
W is selected from $C_1$-$C_{10}$ alkyl, —$CH_2CH_2(CH_2CH_2O)_mCH_2CH_2$—X—, or —$CH_2$—$CH_2OCH_2CH_2$—Z—Y—$CH_2CH_2OCH_2CH_2$—X—,
wherein m is between 0 and 8, X is selected from CO and NH, Y is selected from $CH_2CH_2OH$, pyrimidine, methoxyphenyl, or a composition with formula

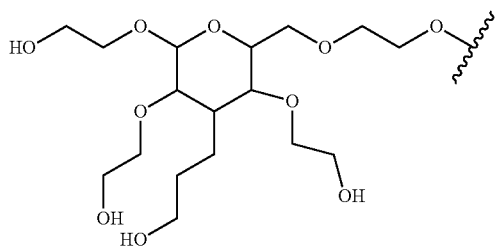 [SMILES: *OCCOCC1OC(OCCO)C(OCCO)C(CCCO)C1OCCO]

Furthermore, the present inventors have identified that particular characteristics of the Z group, namely the fluorophore A molecule and the linker —CO—(W)n, make it possible to maintain the avidity of the antibody or antibody fragment particularly high with respect to the antigen, despite the proximity of the fluorophore to the binding site.

Preferably, the Z group has a total number of hydrogen-binding acceptor atoms (Num_H_Acceptors) of the molecule between 8 and 16, preferably between 10 and 15.

Preferably, the Z group also has a logarithm of the water/octanol partition coefficient (A log P) between 3 and −5.

Preferably, furthermore, the Z group has a surface accessible to the solvent (3DpolarSASA, solvent accessible surface area) of 180 Å$^2$ or more, preferably between 200 and 550 Å$^2$ and/or total polar surface (TPSA, total polar surface area) of 180 Å$^2$ or more, preferably between 180 Å$^2$ and 500 Å$^2$, more preferably between 190 Å$^2$ and 300 Å$^2$.

It cannot be ruled out that the Z group has a combination of the above characteristics.

Consequently, according to one particularly preferred embodiment, the Z group has:
Num_H_Acceptors between 10 and 15;
A log P between 3 and −5;
3DpolarSASA between 200 and 550 Å$^2$
TPSA between 190 Å$^2$ and 300 Å$^2$.

Furthermore, it cannot be ruled out from the scope of the present treatise that the Z group has, alternatively to the above-indicated descriptors, the following characteristics:
Kier flexibility index ((Φ), KierFlex) between 7.5 and 15, preferably between 10 and 12,
water/octanol partition coefficient logarithm (A log P) amounting to 0 or less, preferably between 0 and −10
solvent accessible surface area (3DpolarSASA, solvent accessible surface area) of 300 Å$^2$ or more, preferably between 400 Å$^2$ and 450 Å$^2$, and/or
total polar surface area (TPSA, total polar surface area) of 200 Å$^2$ or more, preferably between 200 Å$^2$ and 220 Å$^2$.

Consequently, according to an alternative preferred embodiment, in the above-mentioned antibody or Fab fragment, the Z group has
KierFlex between 10 and 12;
A log P between 0 and −10;
3DpolarSASA between 400 Å$^2$ and 450 Å$^2$ and
TPSA between 200 Å$^2$ and 220 Å$^2$.

Preferably, in the above antibody or Fab, the group A has a molar extinction coefficient (ε) of not less than 80000 and a quantum yield of not less than 60%.

Preferably, in the above antibody or Fab, the fluorophore group A is selected from between the following groups:
fluorophore CF568
fluorophores derived from xanthene or carbocyanine, preferably with the formula:

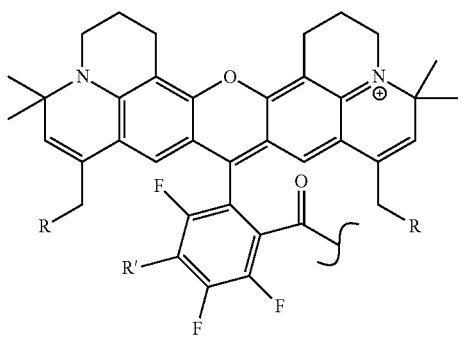

wherein R is a group selected between —OPO$_3$H$_2$ and —OH and R' is selected between —OSO$_3$— and —F;

2-[(1E,3E)-5-[(2Z,3S)-3-(5-methoxy-5-oxopentyl)-3-methyl-5-sulfo-1-(3-sulfopropyl)-2,3-dihydro-1H-indol-2-ylidene]penta-1,3-dien-1-yl]-3,3-dimethyl-5-sulfo-1-(3-sulfopropyl)-3H-indol-2-yl (AF647), having structure

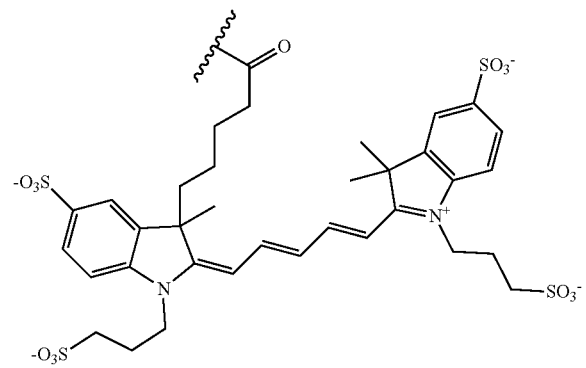

2-(2,2,10,10-tetramethyl-4,8-bis(sulfonatomethyl)-2,10-dihydro-1H-pyrano[3,2-g:5,6-g']diquinolin-11-ium-6-yl)terephthalate (AF568), both regioisomers having structure:

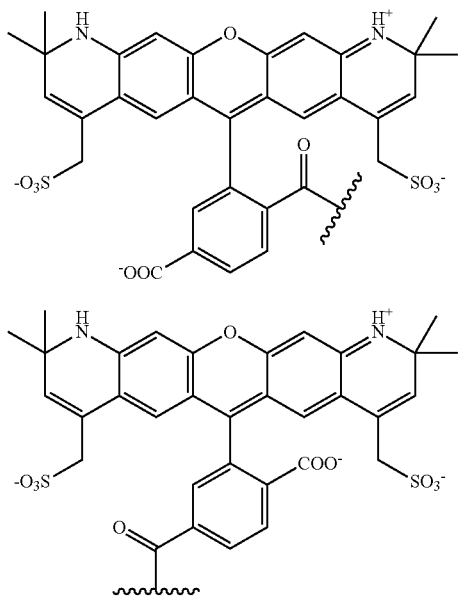

2-[(1E,3Z)-3-[3-(3-carbamoylpropyl)phenyl]-5-[(2Z)-3,3-dimethyl-5-sulfonato-1-(3-sulfonatopropyl)-2,3-dihydro-1H-indol-2-ylidene]penta-1,3-dien-1-yl]-5-chloro-3,3-dimethyl-7-(3-sulfonatopropyl)-3H-pyrrolo[2,3-b]pyridin-7-ium;

2-[(E)-2-[(3E)-3-{2-[(2Z)-1-(5-carbamoylpentyl)-3,3-dimethyl-5-sulfonato-2,3-dihydro-1H-indol-2-ylidene]ethylidene}-2-(4-sulfonatophenoxy)cyclohex-1-en-1-yl]ethenyl]-3,3-dimethyl-1-(4-sulfonatobutyl)-3H-indol-1-ium-5-sulfonate;

(1P)-2-(6-amino-3-iminiumyl-4,5-disulfonate-3H-xanthen-9-yl)-4-carbamoylbenzoate;

1-(5-carbamoylpentyl)-3,3-dimethyl-2-[(1E,3E)-5-[(2Z)-1,3,3-trimethyl-2,3-dihydro-1H-indol-2-ylidene]penta-1,3-dien-1-yl]-3H-indol-1-ium;

2-[(1E,3E)-5-[(2Z)-1-(5-carbamoylpentyl)-3,3-dimethyl-5-sulfonate-2,3-dihydro-1H-indol-2-ylidene]-3-methylpenta-1,3-dien-1-yl]-3,3-dimethyl-1-(4-sulfonatobutyl)-3H-indol-1-ium-5-sulfonate;

2-[(1E,3E)-5-[(1R,2Z)-1-(5-carbamoylpentyl)-3,3-dimethyl-5-sulfonate-2,3-dihydro-1H-indol-1-ium-2-ylidene]penta-1,3-dien-1-yl]-3,3-dimethyl-1-(4-sulfonatobutyl)-3H-indol-1-ium-5-sulfonate;

2-tert-butyl-4-[(1E)-3-[(2E)-1-(5-carbamoylpentyl)-3,3-dimethyl-5-sulfonate-2,3-dihydro-1H-indol-2-ylidene]prop-1-en-1-yl]-9-ethyl-8,8-dimethyl-8H,9H-1λ4-chromeno[7,6-b]pyridin-1-ylium;

4-[(1E)-3-[(2Z,3S)-3-(5-carbamoylpentyl)-3-methyl-6-sulfonate-1-(3-λ)-2,3-dihydro-1H-indol-2-ylidene]prop-1-en-1-yl]-8,8-dimethyl-2-phenyl-6-(sulfonatomethyl)-9-(3-sulfonatopropyl)-8H,9H-1λ4-chromeno[7,6-b]pyridin-1-ylium;

2-tert-butyl-4-[(1E,3E)-5-[(2E)-1-(5-carbamoylpentyl)-3,3-dimethyl-5-sulfonato-2,3-dihydro-1H-indol-2-ylidene]penta-1,3-dien-1-yl]-7-(diethylamino)-1λ4-chromen-1-ylium;

N,N-dimethyl-4-[(2E)-1,5,5-tris[4-(dimethylamino)phenyl]penta-2,4-dien-1-ylidene]cyclohexa-2,5-dien-1-iminium;

2-[(1E,3E)-5-[(2Z)-1-(5-carbamoylpentyl)-3,3-dimethyl-5-sulfonate-2,3-dihydro-1H-indol-2-ylidene]penta-1,3-dien-1-yl]-3,3-dimethyl-1-(4-sulfonatobutyl)-3H-indol-1-ium;

28R)-16-{2-[(3-carbamoylpropyl)methyl)carbamoyl]phenyl}-3-oxa-9λ$^5$,23-diazaheptacyclo[17.7.1.1$^{5,9}$.0$^{2,17}$.0$^{4,15}$.0$^{23,27}$.0$^{13,28}$] octacosa-1(27),2(17),4,9,13,15,18-heptaen-9-ylium;

2-[(1E,3E)-5-[(2Z)-1-(5-carbamoylpentyl)-3,3-dimethyl-2,3-dihydro-1H-indol-2-ylidene]penta-1,3-dien-1-yl]-1,3,3-trimethyl-3H-indol-1-ium;

2-[(1E,3E)-5-[(1Z,2R)-1-(5-carbamoylpentylidene)-3,3-dimethyl-2,3-dihydro-1H-1λ$^5$-indol-1-ylium-2-yl]penta-1,3-dien-1-yl]-3,3-dimethyl-1-(4-sulfonatobutyl)-3H-indol-1-ium;

4-carbamoyl-2-[13-(dimethylamino)-5-(dimethyliminiumyl)-2,2-dimethyl-2-silatricyclo[8.4.0.0$^{3,8}$]tetradeca-1(10),3,6,8,11,13-hexaen-9-yl]benzoate; and 2-[(1E,3E)-5-[(2Z)-1-(5-carbamoylpentyl)-3,3-dimethyl-5-sulfonate-2,3-dihydro-1H-indol-2-ylidene]penta-1,3-dien-1-yl]-3,3-dimethyl-1-(4-sulfonatobutyl)-3H-indol-1-ium;

(7S,17R)-12-[4-(methoxycarbonyl)phenyl]-7,8,8,16,16,17-hexamethyl-2-oxa-6,18-diazapentacyclo[11.7.0.0$^{3,11}$.0$^{5,9}$.0$^{15,19}$]icosa-1(13),3,5,9,11,14,19-heptaen-6-ium-4,20-disulfonate(AF532), having structure

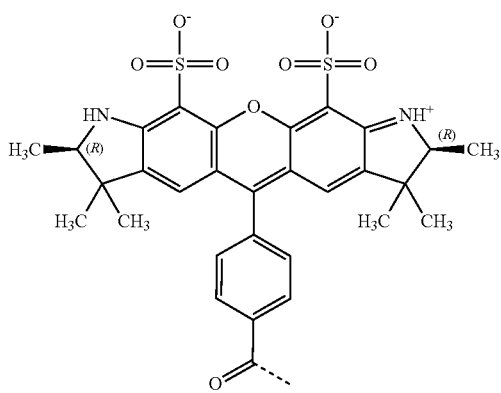

[10,10,22,22-tetramethyl-20-(sulfomethyl)-16-{2,3,4,5-tetrafluoro-6-[(4methoxy-4-oxobutyl)(methyl)carbamoyl]phenyl}-3-oxa-9lambda4,23-diazaheptacyclo[17.7.1.1$^{5,9}$.0$^{2,17}$.0$^{4,15}$.0$^{23,27}$.0$^{13,28}$]octacosa-1,4,9(28),11,13,15,17,19(27),20-nonaen-12-yl]methanesulfonic acid (ASred), having structure

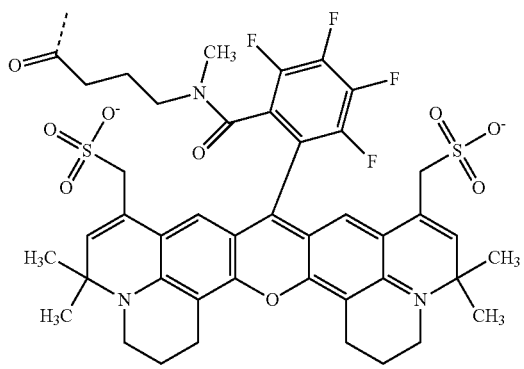

2-({3-[12,20-bis(hydroxymethyl)-10,10,22,22-tetramethyl-3-oxa-9lambda4, 23-diazaheptacyclo[17.7.1.1$^{5,9}$.0$^{2,17}$.0$^{4,15}$.0$^{23,27}$.0$^{13,28}$]octacosa-1,4,9(28),11,13,15,17,19(27),20-onaen-16-yl]-2,5,6-trifluoro-4-[(4-methoxy-4-oxobutyl)(methyl)carbamoyl]phenyl}sulfanyl)ethane-1-sulfonic acid (S635), having structure

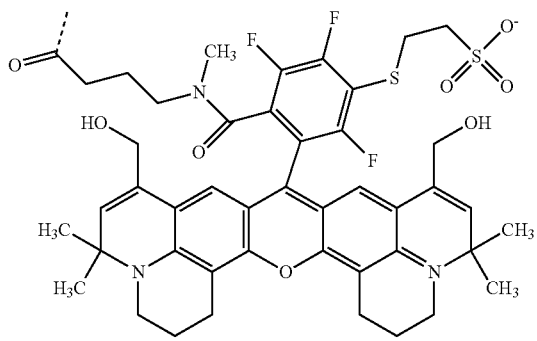

({10,10,22,22-tetramethyl-20-[(phosphonooxy)methyl]-16-{2,3,4,5-tetrafluoro-6-[(4-methoxy-4-oxobutyl)(methyl)carbamoyl]phenyl}-3-oxa-9lambda4,2 3-diazaheptacyclo[17.7.1.1$^{5,9}$.0$^{2,17}$.0$^{4,15}$.0$^{23,27}$.0$^{13,28}$]octacosa-1,4,9(28),11,13, 15,17,19(27),20-nonaen-12-yl}methoxy)phosphonic acid (ABBERIOR star 635P), having structure

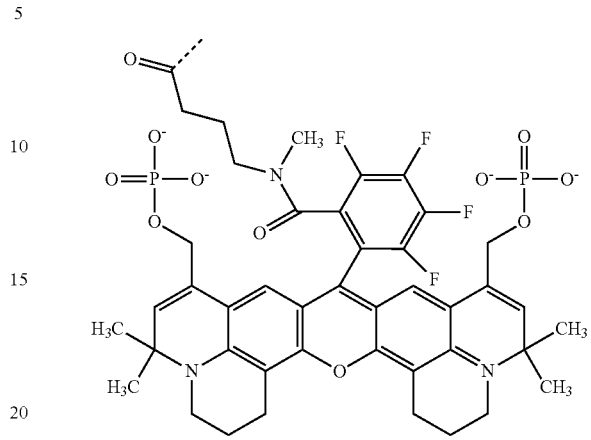

Particularly preferred among these are groups A chosen in the group consisting of: CF568, AF647, AF568, AF532, Asred, S635 and ABBERIOR star 635P more preferably between AF647 and AF568.

As will be demonstrated in the experimental examples that follow, fluorophores which do not have the values of KierFlex, A log P, according to the above-indicated invention, have proven to be not functional, such as e.g. CF647, ATTO590 having structure

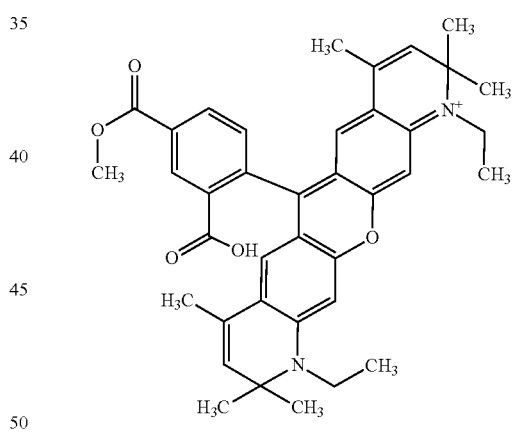

and ATTO647 having structure

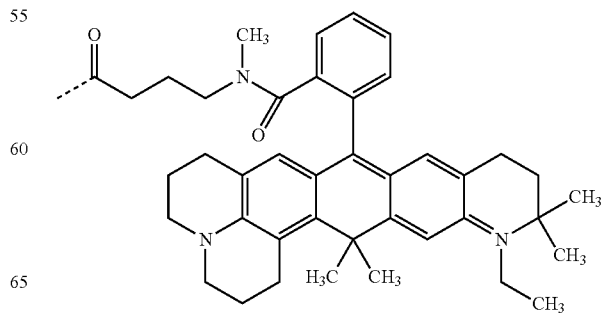

and ATTO565, having structure

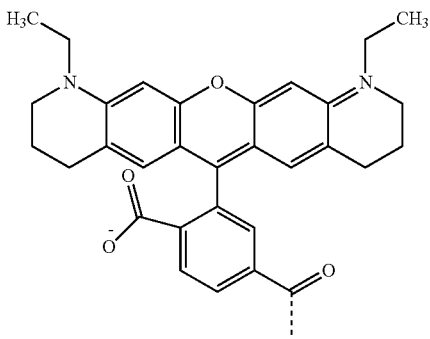

and ATTO647N, having structure

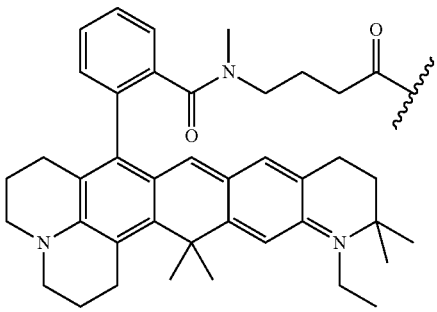

As noted, the antibody or Fab according to the present invention has particular advantages when used in fluorescence microscopy techniques. In fact, compared to traditional fluorescent probes, it allows obtaining a higher specificity and resolution capacity. This makes these reagents particularly suitable for use in super-resolution confocal fluorescence techniques, wherein it is possible to benefit at most from a significant increase in potential resolution (up to 5 times) thanks to the reduced distance between the antigen of interest and the fluorophore.

The use of the probe is therefore mainly intended for biomedical research and for theranostics. On the contrary, the use of some commercial immunoconjugates is purely therapeutic, or, however, if intended for diagnostic use, their administration for human use is foreseen, as described in Oncogenesis (2007; 26, 3734-3744). Therefore, the use of the antibodies and Fab of the invention of the reagents covered by this patent is to be considered exclusively for ex-vivo use.

Therefore, a second object of the present invention is the use of an antibody or a Fab in accordance with the first object of the invention as an immunofluorescent probe, preferably by direct immunofluorescence, in fluorescence microscopy techniques, preferably super resolution confocal fluorescence microscopy.

The third object of the present invention is a method for the preparation of the above antibody or Fab antibody fragment, comprising the reaction between an antibody or Fab fragment and a molecule comprising a fluorophore group A and a —COOB group, and in which group B is a group having electrophile characteristics able to react with nucleophile protein groups, preferably selected from 1-pyrrolidinyl-2.5-dione and 1-pyrrolidinyl-3-sulfonyl-2.5-dione.

Preferably, this method envisages the reaction between an antibody or Fab fragment and a Z molecule with formula A-(W)$_n$-CO—O—B, wherein
n is 0 or 1,
A is a fluorophore group,
W is chosen among $C_1$-$C_{10}$ alkyl, —$CH_2CH_2(CH_2CH_2O)_mCH_2CH_2$—X—, or —$CH_2$—$CH_2OCH_2CH_2$—ZY—$CH_2CH_2O$¬$CH_2CH_2$—X—, wherein m is between 0 and 8, X is chosen between CO and NH, Y is chosen between $CH_2CH_2OH$, pyrimidine, preferably 2.3 pyrimidine-1ll, methoxyphenyl, preferably param-ethoxyphenyl or a compound with formula

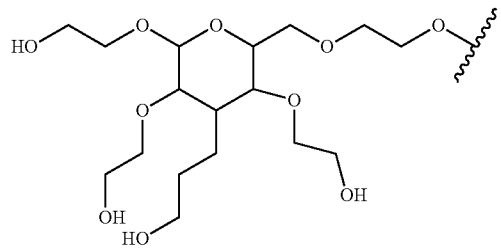 [SMILES: *OCCOCC1OC(OCCO)C(OCCO)C(CCCO)C1OCCO]

and group B is an electrophilic group able to react with nucleophile protein groups, preferably selected from 1-pyrrolidinyl-2.5-dione and 1-pyrrolidinyl-3-sulfonyl-2.5-dione.
having respective formulas

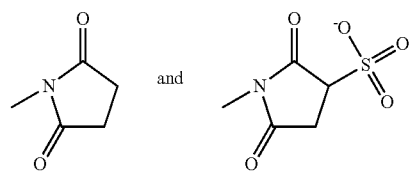

According to a preferred embodiment, the method of the invention, after the reaction between said antibody and said molecule, provides for a stage wherein the reaction product is incubated for a period of time of at least 10 minutes, preferably first of all at a temperature of 37° C. preferably for at least 10 minutes, preferably between 10 and 30 minutes, then at a temperature of 4° C. preferably for a period of at least 8 hours, more preferably between 8 and 15 hours, more preferably 12 hours in the presence of a low molecular weight water-soluble primary amino at a concentration preferably of at least 0.3M, preferably between 0.3M and 5M, more preferably between 0.3 and 3M, more preferably 2M, and a surfactant at a quantity preferably of at least 0.1% by volume, preferably between 0.1% and 1% by volume.

Preferably the above method comprises the following stages:
a) Preparation of a solution of said antibody or Fab fragment in a buffer with a pH between 6 and 8, preferably between 6 and 7.5, more preferably 6.5. Preferably, said buffer is chosen among MES, HEPES and phosphate;
b) Preparation of a solution of a molecule comprising a fluorophore group A and a —COOB group as defined above, in the minimum necessary quantity of an anhydrous organic solvent, preferably chosen between DMSO and DMF;
c) Mixing of the two solutions prepared in a) and b). Preferably, the two solutions are mixed slowly, in the dark and at a temperature between 20 and 38° C., preferably between 25 and 37° C. preferably for a period of at least 10 minutes, more preferably between 15 and 120 minutes, more preferably for 60 minutes. The two solutions are preferably mixed in such a ratio that the ratio number of equivalents of the antibody or Fab and that of the molecule containing the fluorophore is between 0.5 and 2, preferably 1.

d) Addition to the solution resulting from stage c) of an aqueous solution, a water-soluble primary amino, and a surfactant, preferably in such quantity as to obtain a final concentration of primary amino of at least 0.3M, preferably between 0.3 M and 5 M, more preferably between 0.3 and 3M, more preferably of 2M and at least 0.1% by volume of surfactant, more preferably between 0.1% and 1% by volume and a pH between 8 and 10, preferably 8.6, and incubation for at least 10 minutes of the mixture so obtained. Preferably, the mixture resulting from stage d) is first incubated at a temperature of 37° C. for at least 10 minutes, preferably between 10 and 30 minutes, then at a temperature of 4° C. preferably for a period of at least 8 hours, more preferably between 8 and 15 hours, more preferably 12 hours.

Preferably, between the stages c) and d) or, after the stage d), the method also comprises the incubation of the mixture of stage c) or d) first at a temperature between 20 and 38° C., preferably between 25 and 37° C., for a period preferably of at least 5 minutes, preferably between 10 and 20 minutes, more preferably of 15 minutes and then at a temperature between 4° and 20° C. for a period preferably of at least 1 hour, more preferably between 5 and 15 hours, even more preferably of 12 hours.

In this method, the primary water-soluble amino of stage d) should preferably be chosen between ethanolamine or glycine.

Preferably, including in combination with the embodiments mentioned above, in the aforementioned method the surfactant is a non-ionic surfactant, preferably chosen among those containing one or more polyethylene glycol units, such as, e.g., TritonX and Tween-20; even more preferably it is TritonX, which in addition to the polyethylene glycol units also possesses a hydrophobic fragment, consisting of an aryl-4-(1,1,3,3-tetramethyl butyl) type hydrocarbon group. Preferably, in the above method the ratio in moles between the antibody or the Fab fragment and the molecule A-$(CH_2)_n$—CO—O—B is between 2 and 4 for an interval of concentration of antibody or Fab between 2.5-4.0 mg/mL.

Preferably, the above method also comprises a stage e) wherein the antibody or the Fab bonded to linker and fluorophore obtained by the stage d) is purified. Preferably said stage e) comprises a purification by chromatography with molecular exclusion, and the identification of the fractions containing the fluorescent conjugate is by means of chromatography on thin layer acquired by laser scanning.

The Fab fragment used in the method according to the present invention can be obtained by means of techniques well known to the expert in the sector, e.g., by digestion of an antibody with papain or ficin.

EXAMPLES

Example 1—Preparation of Fab Fragments

1a—Preparation of Fab Obtained from a Polyclonal Rabbit Antibody Directed to an Intra-Cellular Protein, C-Terminal-Binding Protein/Brefeldin A-ADP Ribosylated Substrate (CtBP/BARS)

The starting product for the whole procedure was polyclonal rabbit antibody directed against the CtBP/BARS protein and obtained from a commercial formulation (IgG 50-200 µg, 50% glycerol by volume, 0.1-1 mL physiological buffer at pH 6.80-7.20, bovine albumin 0.1% by weight, 5 mM sodium azide) or rabbit serum.

The antibody was dialyzed against 20 mM phosphate buffer at pH 7.00 and incubated for 12 hours at 4° C. with 200 mL of resin sepharose conjugated to protein A. The heterogeneous mixture was mixed by slow overturning and then washed with 5 volumes of 20 mM phosphate buffer at pH 7.00. The antibody was eluted from the resin by the addition of 3 volumes of 100 mM citrate buffer at pH 2.80. The eluate was immediately neutralized during elution with 0.5 volumes of 1 M borate buffer at pH 9.00. The product obtained was dialyzed against 20 mM phosphate buffer at pH 6.50 and concentrated up to 125 µL. 3.12 µg of papain immobilized on agarose were suspended in 12.5 µL of phosphate buffer at pH 7.00 containing 25 mM hydrochloride cysteine and 25 mM sodium EDTA, and incubated with 125 µL of antibody obtained from the previous process and agitated by overturning for 5 hours at 37° C. The supernatant was separated from the resin by filtration and incubated for 10 minutes with 200 µL protein A. The supernatant was again separated from the resin by filtration and extensively dialyzed against phosphate buffer and concentrated up to 4 mg/mL.

1b—Preparation of Fab Obtained from a Monoclonal Mouse Antibody Directed Against the α-Tubuline Intracellular Protein The starting product for the whole procedure consisted of monoclonal mouse antibody directed to the intracellular protein α-tubuline with commercial formula (IgG 50-200 µg, 50% glycerol volume, 0.1-1 mL physiological buffer at pH 6.80-7.20, bovine albumin 0.1% by weight, 5 mM sodium azide) or ascite fluid. The antibody was dialyzed against 20 mM phosphate buffer at pH 9.00 with 1.5 M NaCl and incubated for 12 hours at 4° C. with 200 µL resin sepharose conjugated with protein A. The heterogeneous mixture was mixed by slow overturning and then washed with 5 volumes of 20 mM phosphate buffer at pH 9.00 with 1.5 M NaCl. The antibody was eluted from the resin by the addition of 3 volumes of 100 mM citrate buffer at pH 2.80. The eluate was immediately neutralized during elution with 0.5 volumes of 1 M borate buffer at pH 9.00. The product obtained was dialyzed against 20 mM phosphate buffer at pH 6.50 and concentrated up to 125 µL. 3.12 µg of ficin immobilized on agarose were suspended in 12.5 µL of phosphate buffer at pH 7.00 containing 25 mM hydrochloride cysteine and 25 mM sodium EDTA, and incubated with 125 IL of antibody obtained from the previous process and agitated by overturning for 5 hours at 37° C. The supernatant was separated from the resin by filtration and incubated for 10 minutes with 200 µL protein A. The supernatant was again separated from the resin by filtration and extensively dialyzed against phosphate buffer and concentrated up to 4 mg/mL.

1c—Preparation of Fab Obtained from a Polyclonal Rabbit Antibody Directed to the Protein A-Kinase Anchoring Protein 9 (AKAP9)

Such Fab was obtained by applying the operating methods described in example 1a.

Example 2—Characterization of Fluorophores

The values were measured of Kier, A log P. TPSA e 3DploarSASA and Num_H_Acceptors of the following fluorophores AF568, AF647, CF568, AF532, Asred, S635, ATTO565, ABBERIOR star 635P, ATTO590, ATTO647, ATTO647N.

Specifically: the Kier flexibility index ($\Phi$) and the polar surface area (TPSA) were calculated using Spartan '15 software (Wavefunction Inc., Pipeline Pilot 2016 Biovia, MOE, CCG); the water/octanol partition coefficient (A log P) logarithm was calculated as described above, using the parameters shown on table 1 published in Ghose, A. K.; et al., mentioned above; the surface area of the 3DpolarSASA solvent-accessible molecule was calculated as described above, using the parameters shown on table I published in Ferrara P. et al., mentioned above; the number of hydrogen-binding acceptor atoms (Num_H_Acceptors) was calculated using Pipeline Pilot software (Dassault Systèmes BIOVIA, Pipeline Pilot, R2 version, San Diego: Dassault Systèmes, 2018—Warr W. A. (2012) Scientific workflow systems: pipeline Pilot and KNIME. J. Comput. Aided Mol. Des., 26, 801-804)

For a finer analysis of the chemical-physical properties of the molecules under examination, these have been standardized with a multi-step procedure which provides for:
  i) construction in silico of the molecule in 3-D;
  ii) completion of the molecule with a methyl ester (replacing FAB);
  iii) optimization of the state of protonation/deprotonation of the ionizable groups at a pH of 7.4, (OPLS3, Schrödinger, Inc., New York, NY, 2013);
  iv) conformational analysis using the MCMM method (Chang, G., Guida, W. C., and Still, W. C. (1989) J Am Chem Soc 111, 4379-4386) and selection of the energetically favored conformer. Thus optimized, the molecules were analyzed.

The values obtained for each of the fluorophores are as follows:
  CF568: KierFlex 9.17; A log P −0.219; 3DpPolarSASA 214.048 Å$^2$ and TPSA 210.51 Å$^2$; Num_H_Acceptors 11
  AF532: KierFlex 6.61; A log P −0.577; 3DpPolarSASA 246,006 Å$^2$ and TPSA 192.68 Å$^2$; Num_H_Acceptors 10
  Asred: KierFlex 10.98; A log P 1.408; 3DpPolarSASA 189.951 Å$^2$ and TPSA 193.24 Å$^2$; Num_H_Acceptors 11
  S635: KierFlex 11.81; A log P 3.506; 3DpPolarSASA 235.506 Å$^2$ and TPSA 193.24 Å$^2$; Num_H_Acceptors 11
  AF647: KierFlex 13.76; A log P −4.428; 3DpPolarSASA 541.24 Å$^2$ and TPSA 294.87 Å$^2$, Num_H_Acceptors 15
  ABERRIOR Star 635P: KierFlex 12.13; A log P 1.512; 3DpPolarSASA 329.16 Å$^2$ and TPSA 226.55 Å$^2$; Num_H_Acceptors 13
  ACT 590: KierFlex 9.18; A log P 5.36; 3DpPolarSASA 147.00 Å$^2$ and TPSA 81.91 Å$^2$; Num_H_Acceptors 6
  ACT 647: KierFlex 8.38; A log P 7.40; 3DpPolarSASA 46.73 Å$^2$ and TPSA 52.86 Å$^2$; Num_H_Acceptors 4
  ACT 565: KierFlex 6.66, A log P 3.93; 3DpPolarSASA 135.06 Å$^2$ and TPSA 81.91 Å$^2$; Num_H_Acceptors 6
  ACT 647N: KierFlex 8.38, A log P 7.54; 3DpPolarSASA 44.16 Å$^2$ and TPSA 52.86 Å$^2$; Num_H_Acceptors 4

Example 3—Marking of the Fab Fragments

3a—Fab Marking Obtained in the Example 1a by Means of Fluorophore CF568

Two solutions were prepared.

The first comprised 10 µg of Fab prepared as described in the example 1a in 2.5 µl of 100 mM phosphate buffer at pH 6.50.

The second comprised $8^{-10}$ moles of succinimidyl ester of the fluorophore CF568 in 200 µL of anhydrous DMF and the concentration of fluorophore of the solution was checked by means of spectrophotometry in the visible (Principles of Fluorescence Spectroscopy Third Edition, Joseph R. Lakowicz). The two solutions were slowly mixed and incubated at 37° C. in the dark for an hour.

To the resulting mixture were added 80 µl of an aqueous solution at pH 8.6 containing 2M ethanolamine and 0.1% by volume of Tween 20, which was first kept in the dark at 37° C. for 15 minutes and then at 4° C. throughout the night. The separation of the fluorescent bio-conjugate from the excess of free fluorophore was carried out by means of molecular-exclusion chromatography (Sephadex G25 Fine, GE Healthcare), and the identification of the eluted fractions containing the fluorescent conjugate was carried out by means of thin layer chromatography using laser scanning, the absence of the free probe was verified by means of laser scanning. In detail, the product purified by chromatography was eluted in fractions of 50 microliters. 450 nanoliters of each fraction were loaded onto reverse phase TLC (C18) and the plate developed in $H_2O/CH_3CN$ eluent (1:1 vol/vol) with the addition of 0.01% by volume of an ammonia-saturated aqueous solution. The plate was dried in the dark and at room temperature and then scanned with an Amersham Typhoon Imaging Systems reader.

The acquisition conditions were as follows: laser line at 561 nm or 633 nm; acquisition bands: 580 nm with 30 nm bandwidth, 680 nm with 30 nm bandwidth. The scan proceeded over an area of 5 cm×5 cm, with a pixel size of 100 micron$^2$ and the filtered emission was detected by means of a phototube set at 450 volts. The fractions in which spots at RF=0 were detected were collected and processed for the next step. The fractions with spots at RF=0 and RF=0.8 or only at RF=0.8 were discarded.

The Fab's degree of marking, quantized by visible UV spectrophotometry, was found to be between 1.8 and 2.2. The algebraic expression used for the calculation of the degree of marking (DOL) is as follows:

$$DOL = \frac{A_{max}\varepsilon_{prot}}{(A_{280} - A_{max}C_{280})\varepsilon_{max}}$$

where the values $A_{max}$ and $A_{280}$ indicate the maximum intensity recorded in the fluorophore absorption region and the maximum intensity recorded in the protein region respectively: such values are directly obtained from the UV-VIS spectrum for each conjugate. Diversely, the value $\varepsilon_{prot}$ is estimated at around 71000 M$^{-1}$cm$^{-1}$, while $C_{280}$ and $\varepsilon_{max}$ are provided by the producer of the fluorescent molecule.

The conjugate was stabilized by the addition of 20 μL of an aqueous solution of 0.1% albumin by weight and 5 mM sodium azide, and brought to a storage and use concentration of 0.1 mg/mL using a vacuum centrifugal evaporator.

where the values $A_{max}$ and $A_{280}$ indicate the maximum intensity recorded in the fluorophore absorption region and the maximum intensity recorded in the protein region respectively: such values are directly obtained from the UV-VIS spectrum for each conjugate. Diversely, the value $\varepsilon_{prot}$ is estimated at around 71000 M$^{-1}$cm$^{-1}$, while $C_{280}$ and $\varepsilon_{max}$ are provided by the producer of the fluorescent molecule.

The conjugate was stabilized by the addition of 20 μL of an aqueous solution of 0.1% albumin by weight and 5 mM sodium azide, and brought to a storage and use concentration of 0.1 mg/mL using a vacuum centrifugal evaporator.

3b—Fab Marking Obtained in the Example 1a by Means of Fluorophore AF647

To mark the Fab obtained in the example 1a by means of fluorophore AF647, the procedure was that described in the example 3a.

3c—Fab Marking Obtained in the Example 1b by Means of Fluorophore CF568

To mark the Fab obtained in the example 1b by means of fluorophore CF568, the procedure was that described in the example 3a.

3d—Fab Marking Obtained in the Example 1b by Means of Fluorophore AF647

To mark the Fab obtained in the example 1b by means of fluorophore AF647, the procedure was that described in the example 3a.

3e—Fab Marking Obtained in the Example 1c by Means of Fluorophore CF647

To mark the Fab obtained in the example 1c by means of fluorophore CF647, the procedure was that described in the example 3a.

3f—Marked Fab Marking Obtained in the Example 3c by Means of Fluorophore AlexaFluo488

To mark the marked Fab obtained in the example 3c by means of fluorophore AlexaFluo488, the procedure was that described in the example 3a.

3g—Marked Fab Marking Obtained in the Example 3d by Means of Fluorophore AlexaFluo488

To mark the marked Fab obtained in the example 3d by means of fluorophore AlexaFluo488, the procedure was that described in the example 3a.

3h—Fab Marking Obtained in the Example 1b by Means of Fluorophore AF 532

To mark the Fab obtained in the example 1b by means of fluorophore AF 532, the procedure was that described in the example 3a.

3i—Marked Fab Marking Obtained in the Example 1b by Means of Fluorophore Aberrior Star 635P To mark the marked Fab obtained in the example 1b by means of fluorophore Aberrior star 635P, the procedure was that described in the example 3a.

Example 4—Confocal Microscopy Analysis

Confocal microscopy experiments were conducted using the fluorescent Fabs obtained in the example 3a (INV), 3b (INV), 3c (INV) and 3e (CONTROL) respectively.

In particular, HeLa were fixed in formaldehyde, neutralized and permeabilized with a solution of 50 mM ammonium chloride, saponin of 0.05% by weight and incubated with a bovine albumin solution of 0.1% by weight. The samples were then left to hybridize with 15 μL of a phosphate buffer containing 0.05% saponin and 0.1% albumin by weight and 150 ng of the aforementioned fluorescent Fabs. The excess marker was washed with 1 mL of saline phosphate buffer (PBS) at pH 6.80-7.20 and mounted on 20 μL of Mowiol®.

The microscope used is an inverted confocal Leica SP5-II (Leica Microsystems, Milan, Italy). Cellular samples were included in Mowiol polymer on fluorescence slides, 0.7 mm thick. The images were taken from a 100× oil-immersed lens with a numerical aperture of 1.40 (Leica Microsystems). The excitation of the fluorophores was obtained by means of a laser line at 561 nm and 647 nm and by means of a white pulsed emission laser source (SuperK, Leica) respectively. The fluorescent emissions of each fluorophore were filtered by means of AOBS in a range from 560 nm to 650 nm.

In the images obtained with Fab from rabbit polyclonal directed against the BARS protein marked with CF568 fluorophore, prepared as described in the example 3a (INV), it is possible to observe nuclear and Golgi organelle staining, and drastically lower cytosolic staining (see FIG. 1A and FIG. 1Abis, which refer to images obtained with Fab marked by reaction with 1-pyrrolidinil, 2.5-dione and 1-pyrrolidinil succinimide ester, 3 sulfonyl 2.5-dione, respectively). The location of the fluorescent fragment is in perfect agreement with the data obtained by indirect immunofluorescence.

In the images obtained with Fab from rabbit polyclonal directed against the BARS protein marked with fluorophore AF647, prepared as described in example 3b (INV), it is possible to observe nuclear and Golgi organelle staining, and a drastically lower cytosolic staining (see FIG. 1B and FIG. 1Bbis, which refer to images obtained with Fab marked by reaction with 1-pyrrolidinil, 2.5-dione and 1-pyrrolidinil succinimide ester, 3 sulfonyl 2.5-dione, respectively). Furthermore, the intensity of the signals is lower than that obtained in the example 3a (see FIG. 1A and FIG. 1Abis), congruently to the lower quantum yield of the fluorophore used. The localization of the fluorescent fragment is in this case also in perfect agreement with the data obtained by indirect immunofluorescence.

In the images obtained with Fab from mouse monoclonal directed against the alpha tubulin protein marked with CF568 fluorophore, prepared as described in example 3c (INV), a cytoskeleton staining can be observed, specifically a staining of the microtubules (see FIG. 2A and FIG. 2Abis, which refer to images obtained with Fab marked by reaction with succinimide esters 1-pyrrolidinil, 2.5-dione and 1-pyrrolidinil, 3 sulfonyl 2.5-dione, respectively). The location of the fluorescent fragment is in perfect agreement with the data obtained by indirect immunofluorescence.

In the images obtained with Fab from rabbit polyclonal directed against the protein AKAP9 marked with CF647 fluorophore, prepared as described in the example 3e (COMPARISON), it is possible to observe an incorrect localization of the fluorescent conjugate, as nuclear staining is observed in addition to cytosolic and/or mitochondrial staining (see FIG. 2B and FIG. 2Bbis, which refer to images obtained with Fab marked by reaction with the succinimide ester 1-pyrrolidinil, 2.5-dione and 1-pyrrolidinil, 3 sulfonyl 2.5-dione, respectively). The localization of the fluorescent fragment is in total disagreement with the data obtained from literature and by indirect immunofluorescence, which instead report a localization of the target protein only on the Golgi organelle.

As can be seen from the results of the above examples, Fabs conjugated through a linker with specific length and flexibility characteristics to CF568 and AF647 fluorophores, having specific characteristics such as: KierFlex between 7.5 and 15; A log P below or equal to 0; 3DpolarSASA equal or higher than 300, are stable, have uniform characteristics in terms of positioning of fluorophore and maintain avidity for the antigen. In particular, the 3D polar SASA parameter, which provides for the degree of hydration of the molecule, is responsible for greater stabilization of the conjugate, less tendency to aggregate because it is hydrated and better emissive behavior due to increased solvation. Furthermore, the decreased tendency to interact with parts of the fragment also translates into a significant increase in avidity because the fluorophores do not collapse on the recognition regions of the Fab.

Example 5—Comparison Between Conventional Marking (Indirect Immunofluorescence) and that Produced by Fluorescent Fabs, to which the Present Invention Relates Conventional marking was performed with mouse monoclonal antibody fragment, type IgG1, in HeLa human cells fixed, permeabilized and subjected to a common immunofluorescence procedure.

HeLa human cells were fixed, permeabilized and subjected to an immunofluorescence procedure as described below. The sample preparation procedure is completely similar to indirect immunofluorescence. The cells grew on a 1 cm×1 cm quartz slide, in RPMI medium (Dulbecco) supplemented with 10% in volume of bovine serum, penicillin, glutamine. The cells are fixed by treatment with 4% formaldehyde in buffered saline solution at pH 7.00 for 10 minutes. The excess aldehyde was neutralized with a 50 mM ammonium chloride solution, buffered at pH 7.00. The fixed samples undergo washing in saline phosphate buffer and permeabilized with 0.05% by weight of vegetable saponin solution. The samples were incubated for one hour with Fab directed against the alpha-tubuline protein, conjugated with fluorophore CF568 prepared as described in example 3c (samples 1-3) or fluorophore AF647 prepared as described in example 3d (samples 4-5) and the excess present was removed by 3 washes in saline phosphate buffer. Any non-specific adsorption sites of markers (primary and secondary) in the cell samples were prevented by incubation with 0.1% by weight bovine albumin solution in saline physiological solution.

To each sample was added a commercial probe consisting of the AlexaFluor488 marker conjugated to rabbit polyclonal antibody directed against mouse monoclonal antibody of the IgG1 type.

The signal emitted by the fragment, to which the present invention relates, was detected by means of the acquisition of emission of fluorescence in the wavelength range specific for the type of fluorophore: in the case of CF568, the acquisition range is within the range from 575 nm to 620 nm; while in the case of AF647, the acquisition range is within the range from 660 nm to 700 nm. The control fluorophore, AlexaFluor bound to the secondary antibody directed against the Fab, can be excited separately from the other two, so its emission, collected in the range from 490 nm to 450 nm, if collected only for the time in which it is individually excited, can be considered independent and therefore free of light contamination between the channels. It is therefore possible to make a quantitative and functional comparison between a conventional marking (indirect immunofluorescence) and that produced by fluorescent Fabs, to which the present invention relates.

3 samples were prepared marked with the CF568 probe and with the AlexaFluor488 commercial probe and 2 samples marked with the AF647 probe and with the AlexaFluor488 commercial probe.

Comparing the FIG. 3A with FIGS. 3B, 4A with 4B, 5A with 5B, 6A with 6B and 7A with 7B respectively, we can see not only the complete functionality of the proposed marker, consistently with the calculated data, both for the CF568 probe and for the AF647 probe, but from this analysis also emerges an aspect of considerable importance as regards the functional superiority of the invention.

As can be seen from FIGS. 3B, 4B, 5B, 6B and 7B representing the images in which the signal, emitted by the Fab to which the present invention relates, was detected by means of fluorescence emission acquisition in the wavelength range specific to the CF568 or AF647 fluorophore, the reduced dimensions of the probe to which the present invention relates, about one sixth compared to those of the conventional probe, are not only able to generate a high staining density, but also allow the localization of the probe in cell regions to which the conventional marker does not have access. The area of interest lies in the midbodies.

On the contrary, as can be seen from FIGS. 3A, 4A, 5A, 6A and 7A representing the images in which the signal emitted by the Fab to which the present invention relates was detected by means of fluorescence emission acquisition in the wavelength range specific to the commercial fluorophore AF488, the conventional probe does not have access to the area where the midbodies are located.

These regions are connections between cells which are reduced to a thin filament in the final stages of the cytokinesis process. Responsible for this bottleneck are the actin filaments forming a contractile filament which force the cytoskeleton and, by creating a bottleneck, cause the two daughter cells to separate. In the examples shown below, it can be seen that only the probe to which the patent relates is able to penetrate and indicate, in detail, the morphological state of the above midbodies.

Cell division is currently a process of considerable interest because it is involved in metastatic and neoplastic mechanisms, so the use of the Fab according to the invention to visualize cell compartments which are not visible by traditional marking can be an ideal example of the functional superiority of such reagents in the field of cell imaging.

Therefore such fluorescent Fabs are useful in microscopy techniques and permit obtaining a high level of resolution and visualizing cell compartments not visible with traditional marking.

In this regard, the FIGS. 8A, 8B, 8C, 8D represent a comparison between the images obtained with probes currently on the market and probes in accordance with the present invention.

The samples were incubated for one hour with Fab directed against the α-tubuline protein, conjugated with the fluorophore AF 647 prepared as described in the example 3d.

At the same time, to other samples was added a probe consisting of a commercial anti-α-tubuline antibody conjugated randomly with the fluorophore AF 647.

The signal emitted by the invented fragment (FIGS. 8A, 8B) was compared with the signal emitted by conventionally marked antibodies (FIGS. 8C, 8D) in order to quantify the uncertainty limit by which the α-tubuline is localized and, consequently, to measure the diameter of the microtubule.

Figure 8A:
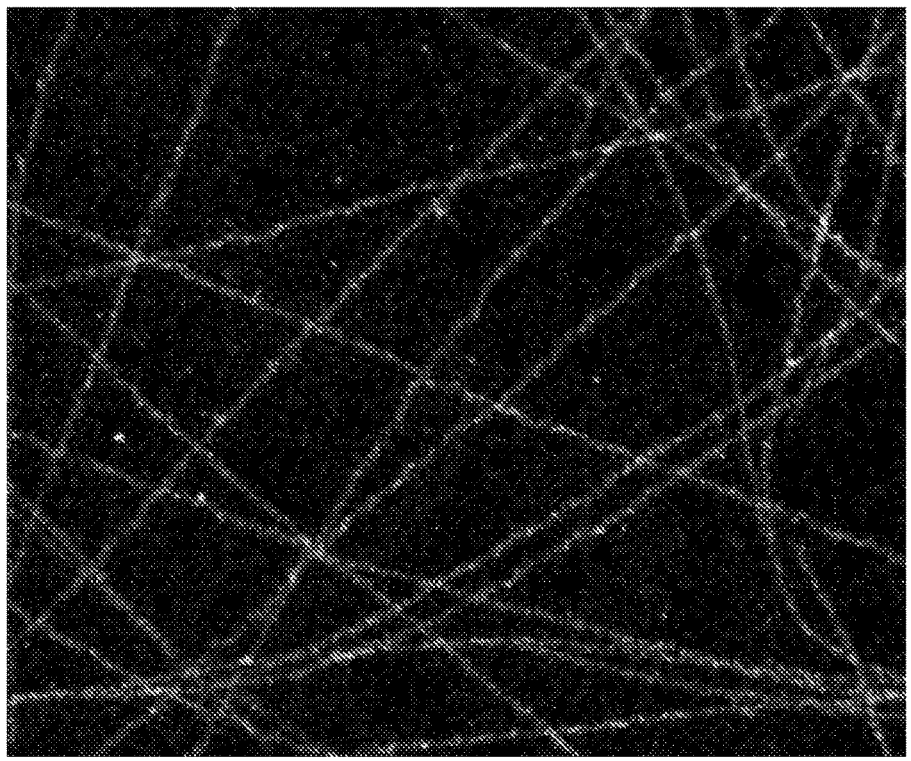
Figure 8B:
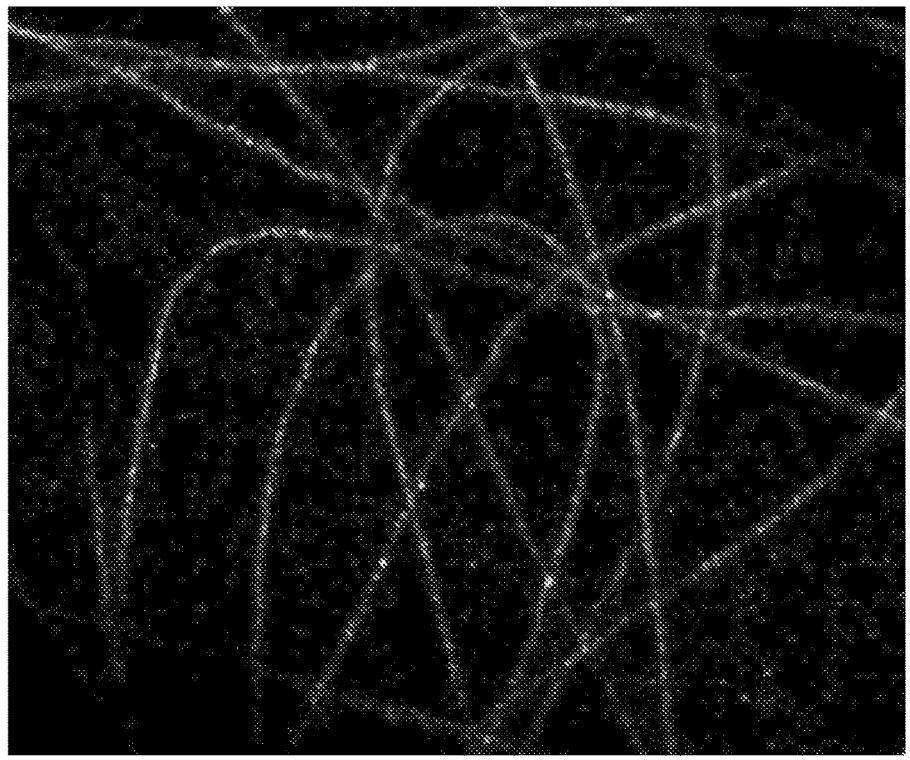
Figure 8C:
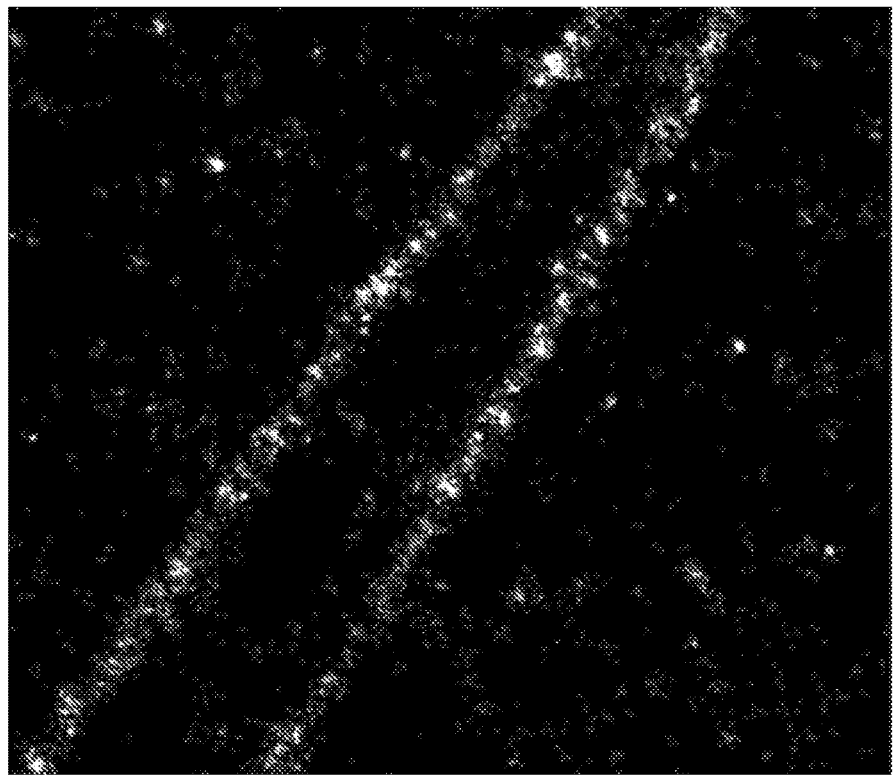
Figure 8D:
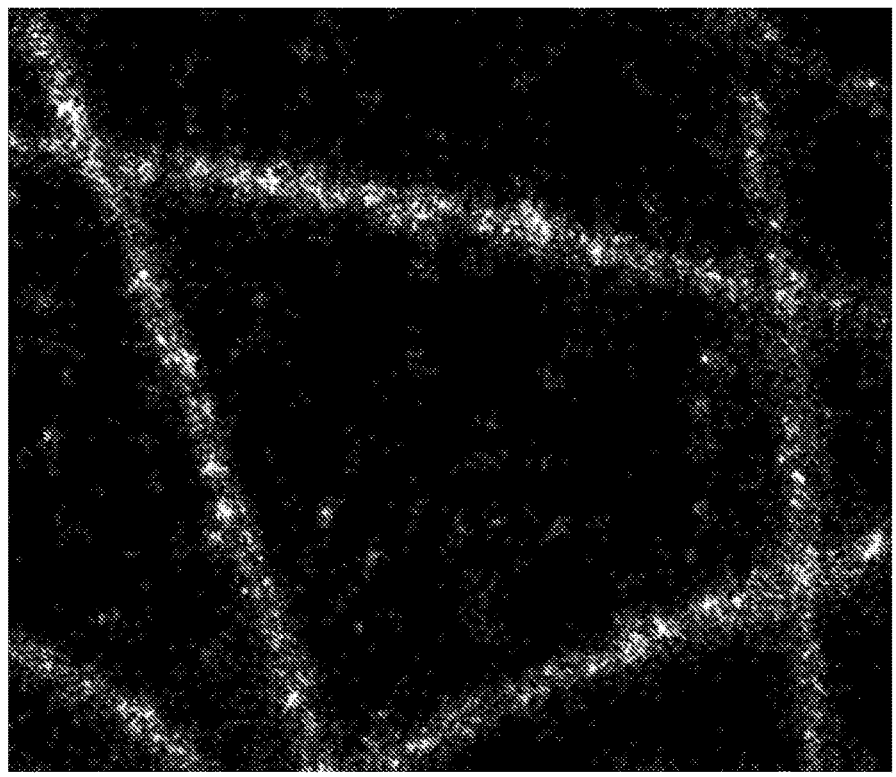

As shown in the FIGS. 8C, 8D, the size of the microtubular section evidenced by the use of conventional antibody is larger than the actual size. This increase is associated with the greater uncertainty of localization caused by the diffusion of the emitted light signal and corresponding to an indefinite region of space within which the uncertainty on the real position of the microtubule is distributed.

On the contrary, as can be seen in FIGS. 8A, 8B which represent the images in which the signal emitted by the Fab to which the invention relates was detected, the smaller microtubular diameter is indicative of a smaller dispersion of the fluorescence emission and, therefore, of a greater resolution limit.

In detail, the distribution of the fluorescent signal along the intersection of the microtubule represents the indetermination of the marking which is significantly lower when the Fab to which the present invention relates is used.

Furthermore, the fact that the Fab to which the present invention relates is positioned at about 1-2 nm from α-tubuline results in a lower dispersion of the fluorescent signal.

From the FIG. 9, the functional superiority can be seen of the present invention in line with the above data. In fact, the mean diameter value for each segment measured is about 2 nm away from the actual value with Fab in accordance with the present invention. On the contrary, localizations obtained with conventional probes (in the figure indicated with Ab) oscillate by about 8 nm around the mean value.

In detail, the mean value recorded through the use of Fab in accordance with the present invention is equal to 28 nm, while the mean value recorded through the use of probes of the conventional type is 42 nm.

Considering the actual diameter of a microtubule equal to 25 nm, it appears evident that the resolution limit has been significantly increased by using probes in accordance with the present invention.

At the same time, as can be seen from the FIG. 10, screening has been developed using 10 fluorophores conventionally used in super-resolution microscopy and having a different structure.

In detail, the loss of affinity of the conjugated Fab towards its antigen can be directly verified by confocal microscopy, evaluating known cellular morphologies.

This analysis showed that four of the ten structures tested prevented the conjugate from binding the antigen; this corresponds to the loss of the expected morphology (in this case the cytoskeleton), as the presence of the fluorophore totally prevents its binding to the antigen.

At the same time, in order to evaluate the influence exerted by the pH reaction values on the possible overlapping of the Fabs behavior with regard to the derivatization of the two categories of amino groups previously described, a study was carried out on the in silico prediction of the relative pKa values (FIG. 10).

As is known, the mean values of the pKs of the terminal amino and ε-amino groups, are around 7.5 and 13 respectively.

Such difference would formally allow discrimination between the various amino groups by simply working on the operating pH. It can be approximately calculated that 3 units of pK of difference (e.g., pK 7.5 against pK 10.5) between a lysine terminal amino group and an ε-amino group, results in a high percentage difference in the state of protonation between the two compared amino groups.

For example, at a pH=7.4 which is close to the pK of the terminal $NH_2$ group, 44.3% of these are deprotonated and available, while only 0.08% of the ε-amino groups are available.

In any case, the simultaneous presence of amino groups (terminal against ε-amine) which compete with regard to a fluorophore functionalized with a succinimide group, requires a realistic evaluation of the percentages of deprotonated amino groups available for conjugation at each pH value around which the request for adequate specificity is satisfied.

The prediction of pKa values of amino groups was performed with a hybrid quantum mechanics/molecular mechanics method (ab initio QM/MM), using two applications, Qsite (Murphy, R. B.; Philipp, D. M.; Friesner, R. A., "A mixed quantum mechanics/molecular mechanics (QM/MM) method for large-scale modeling of chemistry in protein environments," J. Comp. Chem., 2000, 21, 1442-1457; Philipp, D. M.; Friesner, R. A., "Mixed ab initio QM/MM modeling using frozen orbitals and tests with alanine dipeptide and tetrapeptide," J. Comp. Chem., 1999, 20, 1468-1494) and Protein Titration Curve, contained in the program suites Small-Molecule Drug Discovery Suite (Small-Molecule Drug Discovery Suite 2018-2, Schrödinger, LLC, New York, NY, 2018) and Biologics Suite (Biologics Suite 2018-2, Schrödinger, LLC, New York, NY, 2018), respectively.

TABLE 2

| M204 | | |
| --- | --- | --- |
| Amino | Chain-Position | pKa predicted |
| N-term | GLN1H | 7.37 |
| LYS | 42H | 10.35 |
| LYS | 63H | 10.11 |
| LYS | 70H | 9.36 |
| LYS | 78H | 10.34 |
| LYS | 95H | 9.85 |
| LYS | 119H | 10.15 |
| LYS | 145H | 8.43 |
| LYS | 205H | 10.92 |
| LYS | 208H | 10.39 |
| N-term | ASP1L | 7.75 |
| LYS | 22L | 11.24 |
| LYS | 39L | 9.87 |
| LYS | 63L | 9.86 |
| LYS | 109L | 10.37 |
| LYS | MOL | 11.03 |
| LYS | 164L | 11.24 |

TABLE 2-continued

M204

| Amino | Chain-Position | pKa predicted |
|---|---|---|
| LYS | 191L | 11.31 |
| LYS | 196L | 11.4 |

In terms of prediction of pKa values, a first analysis was centered in particular on two antibodies widely used in experimental practice and for which the relative 3-D structure is available:

i) the monoclonal FAB IgG1 isotype k mouse antibody fragment (anti-c-myc clone 9E10, PDB ID: 2OR9—Table 1) and ii) the monoclonal FAB M204 rabbit antibody fragment (Table 2).

TABLE 1

ID: 2OR9

| Amino | Chain-Position | pKa predicted |
|---|---|---|
| N-term | GLU1H | 7.8 |
| LYS | 13H | 10.32 |
| LYS | 19H | 10.18 |
| LYS | 43H | 10.81 |
| LYS | 64H | 11.35 |
| LYS | 75H | 12.04 |
| LYS | 83H | 11.29 |
| LYS | 115H | 10.44 |
| LYS | 143H | 9.19 |
| LYS | 205H | 10.49 |
| LYS | 208H | 11.3 |
| LYS | 209H | 10.29 |
| N-term | ASP1L | 9.96 |
| LYS | 39L | 11.12 |
| LYS | 45L | 8.98 |
| LYS | 92L | 12.3 |
| LYS | 103L | 11.9 |
| LYS | 107L | 10.25 |
| LYS | 142L | 11.59 |
| LYS | 147L | 12.44 |
| LYS | 149L | 11.41 |
| LYS | 169L | 10.45 |
| LYS | 183L | 12.44 |
| LYS | 199L | 11.43 |
| LYS | 207L | 9.92 |

In both cases, the present inventors observed some lysine residues characterized by pKa values which were not between 10 and 13, as expected, but which had lower values below 9, and were therefore not far from those of the terminal amino groups the mean value of which is around 7.5.

A second important observation comes from the analysis of mouse antibody, whose light chain terminal amino group shows, on the contrary, a pKa significantly higher than expected (7.5) at the value of 9.96. These observations have highlighted conditions the occurrence of which is of clear importance to us. The analysis was then extended to predict the pKa values of the amino groups for further 18 antibodies (a total of 20, i.e. approximately 20% of the mouse and rabbit antibodies with known amino acid sequences), the 3D structure of which was determined. These antibodies were selected according to the criterion of maximizing the diversity of the amino-acid sequence, so as to exclude a possible aminoacidic-structural bias (Table 3).

TABLE 3

| Antibody | PDB code | L chain N-term pKa predicted | H chain N-term pKa predicted |
|---|---|---|---|
| A2NHM3 MOUSE | 1CBV | 7.49 | 8.02 |
| ANTI-DINITROPHENYL-SPIN-LABEL FAB | 1BAF | 7.64 | 7.83 |
| Zika specific antibody, ZV-2 | 5KVD | 7.64 | 7.55 |
| blue fluorescent antibody EP2-19G2 | 3CFC | 8.76 | 7.87 |
| monoclonal antibody 2D10 | 5F3J | 8.61 | |
| anti-Francisella tularensis GroEL antibody Ab64 | 4PB9 | 7.83 | 8.05 |
| monoclonal antibody mAb 26-2F | 1H0D | 8.05 | 8.17 |
| monoclonal antibody 4C4 | 1EJ0 | 9.11 | 7.45 |
| OXY-COPE antibody AZ-28 | 1D6V | 8.1 | 7.84 |
| C836 FAB | 3L5W | 8.56 | 7.84 |
| DENV1-E106 Fab | 4L5F | 7.98 | 8.23 |
| 82D6A3 Antithrombotic Antibody | 2ADF | 6.39 | 7.84 |
| S73-2ab | 3HZK | 7.7 | 7.98 |
| CL40/29G12 | 5W0K | 7.63 | 7.92 |
| DsbB-Fab | 2ZUQ | 7.85 | 7.76 |
| anti-uPAR Fab 8B12 | 4QTH | 7.76 | 7.79 |
| AD related fab | 3U0W | 7.52 | 7.94 |
| Fab portion of Olokizumab | 4CNI | 8.7 | 8.04 |

This analysis shows that in most of the FABs considered, the respective pKas of the two chains (H, L) show mean values of around 7.5. However, in a smaller number of cases, as for the above-mentioned anti-c-myc clone 9E10 antibody, one of the two NH2 terminal groups (that of the light chain, L), shows significantly higher pKa values.

When this occurs, it is obvious that the terminal amino group actually available for selective derivatization, e.g. at pH≤7.4, is only 1 (that of the heavy chain).

As for the selectivity of the reaction, this is related to the particular operating pH.

The following example illustrates the case of an FAB characterized by a terminal amino group with pKa=7.8 and an ε-amino group with pKa=8.89, potentially in competition. FIG. 10 shows the titration curves from which the percentage fractions can be evaluated of the free amino groups (in the illustration, $NH_{2\text{-}ter}$) and of the ε-amino groups (in the illustration indicated as $NH_{2\text{-}lysine}$) at every pH.

At the same time, a curve ($NH_{2\text{-}ter}/NH_{2\text{-}lysine}$) is shown which indicates the variations in the $NH_{2\text{-}ter}/NH_{2\text{-}lysine}$ ratio and from which it is possible to select an optimum pH for its maximization.

In accordance with the object of the present invention, it is clear how it is necessary to identify reaction conditions such as to ensure the selectivity of the derivatization reaction of the Fab fragment with an activated fluorophore.

In this regard, the conjugation reaction comprises numerous steps of which only the final one is irreversible and, on the contrary, the others are reversible and governed by equilibrium conditions and by the availability of the reactive substrate, the latter depending on the pH values.

From the study of the reaction of aminolysis of ester, it is clear that the latter proceeds by means of general basic catalysis, making it evident that dynamic reversibility exists only for the first reaction steps (consisting in the deprotonation of the amino group and in the formation of an intermediate tetravalent). The latter, however, irreversibly evolves in the final product by expulsion of the hydroxysuccinimide group followed by a substantially simultaneous formation of the amide link with the fluorophore.

Ultimately, the operating pH can be chosen so as to ensure selectivity with respect to the terminal amino groups without affecting the total yield of the reaction.

The invention claimed is:

1. An Antibody or a Fab fragment, wherein at least one amino group of the N-terminal amino acid of the light chain and/or of the N-terminal amino acid of the heavy chain is bound by an amidic bond to a molecule comprising a fluorophore group A, wherein said bond constitutes at least 70% of the total binding of said molecule to said antibody or said Fab;

wherein said amino group of the N-terminal amino acid of the light chain and/or of the N-terminal amino acid of the heavy chain is bound by an amidic bond to a Z group with formula —CO-A;

wherein said group A is selected from:

fluorophore CF568;

2-[(1E,3E)-5-[(2Z,3S)-3-(5-methoxy-5-oxopentyl)-3-methyl-5-sulfo-1-(3-sulfopropyl)-2,3-dihydro-1H-indol-2-ylidene]penta-1,3-dien-1-yl]-3,3-dimethyl-5-sulfo-1-(3-sulfopropyl)-3H-indol-2-yl (AF647), having structure

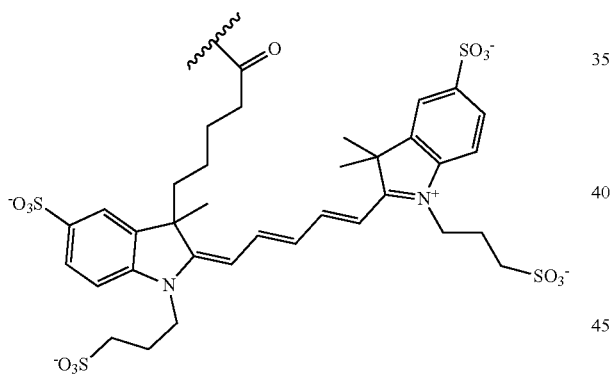

2-(2,2,10,10-tetramethyl-4,8-bis(sulfonatomethyl)-2,10-dihydro-1H-pyrano[3,2-g:5,6-g']diquinolin-11-ium-6-yl)terephthalate (AF568, both regioisomers), having one of the following structures

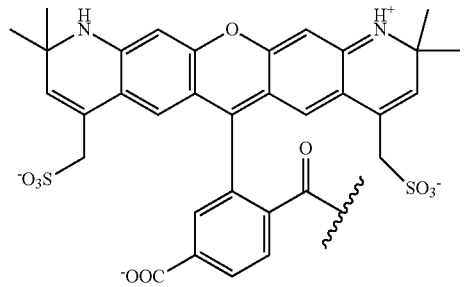

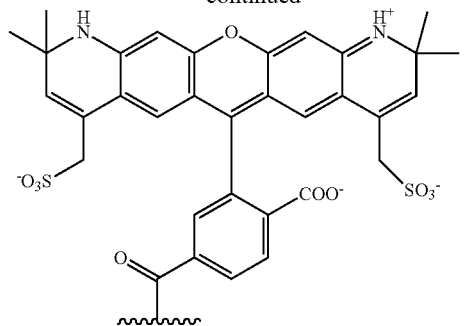

(7S,17R)-12-[4-(methoxycarbonyl)phenyl]-7,8,8,16,16,17-hexamethyl-2-oxa-6,18-diazapentacyclo[11.7.0.$0^{3,11}$.$0^{5,9}$.$0^{15,19}$]icosa-1(13),3,5,9,11,14,19-heptaen-6-ium-4,20-disulfonate (AF532), having structure

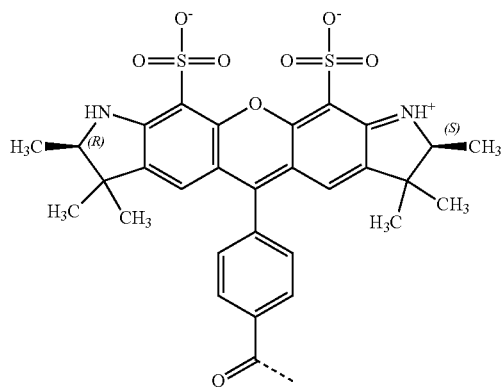

[10,10,22,22-tetramethyl-20-(sulfomethyl)-16-{2,3,4,5-tetrafluoro-6-[(4-methoxy-4-oxobutyl)(methyl)carbamoyl]phenyl}-3-oxa-9lambda4,23-diazaheptacyclo[17.7.1.1$^{5,9}$.$0^{2,17}$.$0^{4,15}$.$0^{23,27}$.$0^{13,28}$]octacosa-1,4,9(28),11,13,15,17,19(27),20-nonaen-12-yl] methanesulfonic acid (ASred), having structure

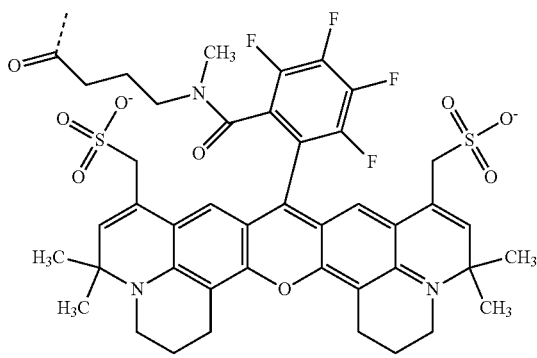

2-({3-[12,20-bis(hydroxymethyl)-10,10,22,22-tetramethyl-3-oxa-9lambda4,23-diazaheptacyclo[17.7.1.1$^{5,9}$.0$^{2,17}$.0$^{4,15}$.0$^{23,27}$.0$^{13,28}$]octacosa-1,4,9(28),11,13,15,17,19(27),20-onaen-16-yl]-2,5,6-trifluoro-4-[(4-methoxy-4-oxobutyl)(methyl)carbamoyl]phenyl}sulfanyl)ethane-1-sulfonic acid (S635), having structure

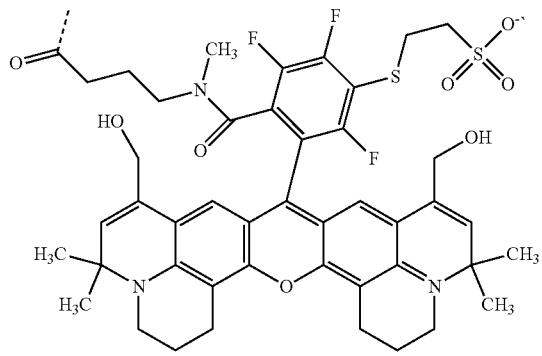

({10,10,22,22-tetramethyl-20-[(phosphonooxy)methyl]-16-{2,3,4,5-tetrafluoro-6-[(4-methoxy-4-oxobutyl)(methyl)carbamoyl]phenyl}-3-oxa-9lambda4,23-diazaheptacyclo[17.7.1.1$^{5,9}$.0$^{2,17}$.0$^{4,15}$.0$^{23,27}$.0$^{13,28}$]octacosa-1,4,9(28),11,13,15,17,19(27),20-nonaen-12-yl}methoxy)phosphonic acid, having structure

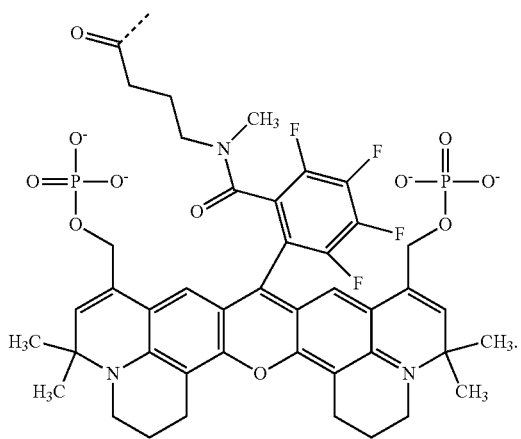

2. The Antibody or the Fab fragment according to claim 1, wherein said antibody is monoclonal or said Fab is obtained from a monoclonal antibody.

3. The Antibody or the Fab fragment according to claim 1, wherein the Z group has a total number of hydrogen-binding acceptors atoms (Num_H_Acceptors) of the molecule between 8 and 16.

4. The Antibody or the Fab fragment according to claim 1, wherein the Z group has a logarithm of the water/octanol partition coefficient (A log P) between 3 and −5.

5. The Antibody or the Fab fragment according to claim 1, wherein the Z group has a surface accessible to the solvent (3DpolarSASA, solvent accessible surface area) of 180 Å$^2$ or more.

6. The Antibody or the Fab fragment according to claim 1, wherein the Z group has:
Kier flexibility index (($\Phi$), KierFlex) between 7.5 and 15,
water/octanol partition coefficient logarithm (A log P) amounting to 0 or less,
solvent accessible surface area (3DpolarSASA, solvent accessible surface area) of 300 Å$^2$ or more, and/or
total polar surface area (TPSA, total polar surface area) of 200 Å$^2$ or more.

7. The Antibody or the Fab fragment according to claim 1, wherein said group A has a molar extinction coefficient ($\varepsilon$) of not less than 80000 and a quantum yield of not less than 60%.

8. The Antibody or the Fab fragment according to claim 1, wherein said antibody is a rabbit polyclonal antibody of the IgG2b type or a mouse monoclonal antibody of the IgG1 type or said Fab fragment is obtained from an antibody selected from a rabbit polyclonal antibody of the IgG2b type or a mouse monoclonal antibody of the IgG1 type.

9. The Fab fragment according to claim 1, obtained from the digestion of an antibody with papain or ficin.

10. A method for the preparation of the antibody or the Fab according to claim 1, comprising the reaction between the antibody or the Fab fragment and a molecule Z—OB comprising a fluorophore group A and a —COOB group, and wherein the group B is a group having electrophile characteristics;
wherein said method comprises the following steps:
a) Preparation of a solution of said antibody or said Fab fragment in a buffer with a pH between 6 and 8;
b) Preparation of a solution of said molecule Z—OB, in a predetermined minimum necessary quantity of an anhydrous organic solvent;
c) Mixing of the two solutions prepared in a) and b), the two solutions are mixed, in the dark and at a temperature between 20° C. and 38° C., the two solutions are mixed in such a ratio that the ratio of equivalents of the antibody or the Fab and that of the molecule containing the fluorophore is between 0.5 and 2;
d) Addition to the solution resulting from step c) of an aqueous solution, a water-soluble primary amine, and a surfactant, in such quantity as to obtain a final concentration of primary amine of at least 0.3M, and incubation for at least 10 minutes of the mixture so obtained, then at a temperature of 4° C.

11. The method according to claim 10, wherein said primary amine is chosen between ethanolamine or glycine.

12. The method according to claim 10, wherein said surfactant is a non-ionic surfactant, chosen among those containing one or more polyethylene glycol units.

13. The Antibody or the Fab fragment according to claim 1, wherein said bond constitutes at least 80%, 85%, 90%, or 98% of the total bond of said molecule to said antibody or said Fab.

14. The Antibody or the Fab fragment according to claim 1, wherein the Z group has a total number of hydrogen-binding acceptors atoms (Num_H_Acceptors) of the molecule between 10 and 15.

15. The Antibody or the Fab fragment according to claim 1, wherein the Z group has a surface accessible to the solvent (3DpolarSASA, solvent accessible surface area) between 200 and 550 Å$^2$ and/or total polar surface (TPSA, total polar surface area) of 180 Å2 or more.

16. The Antibody or the Fab fragment according to claim 1, wherein the Z group has a surface accessible to the solvent (3DpolarSASA, solvent accessible surface area) between 180 Å$^2$ and 500 Å$^2$.

17. The Antibody or the Fab fragment according to claim 1, wherein the Z group has a surface accessible to the solvent (3DpolarSASA, solvent accessible surface area) between 190 Å$^2$ and 300 Å$^2$.

18. The Antibody or the Fab fragment according to claim 1, wherein the Z group has:

Kier flexibility index (($\Phi$), KierFlex) between 10 and 12, water/octanol partition coefficient logarithm (A log P) amounting between 0 and −10, solvent accessible surface area (3DpolarSASA, solvent accessible surface area) between 400 Å$^2$ and 450 Å$^2$, and/or total polar surface area (TPSA, total polar surface area) between 200 Å$^2$ and 220 Å$^2$.

* * * * *